(12) United States Patent
Hong et al.

(10) Patent No.: US 10,141,521 B2
(45) Date of Patent: Nov. 27, 2018

(54) COMPOUND, ORGANIC OPTOELECTRONIC ELEMENT COMPRISING SAME, AND DISPLAY DEVICE

(71) Applicant: SAMSUNG SDI CO., LTD., Yongin-si, Gyeonggi-do (KR)

(72) Inventors: Jin-Seok Hong, Suwon-si (KR); Eun-Sun Yu, Suwon-si (KR); Dong-Kyu Ryu, Suwon-si (KR); Han-Ill Lee, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 375 days.

(21) Appl. No.: 14/783,499

(22) PCT Filed: Nov. 4, 2013

(86) PCT No.: PCT/KR2013/009896
§ 371 (c)(1),
(2) Date: Oct. 9, 2015

(87) PCT Pub. No.: WO2015/005536
PCT Pub. Date: Jan. 15, 2015

(65) Prior Publication Data
US 2016/0056394 A1 Feb. 25, 2016

(30) Foreign Application Priority Data
Jul. 11, 2013 (KR) .................. 10-2013-0081722

(51) Int. Cl.
*H01L 51/50* (2006.01)
*H01L 51/00* (2006.01)
(Continued)

(52) U.S. Cl.
CPC ........ *H01L 51/0072* (2013.01); *C07D 471/04* (2013.01); *C07D 471/06* (2013.01);
(Continued)

(58) Field of Classification Search
None
See application file for complete search history.

(56) References Cited

U.S. PATENT DOCUMENTS

| 4,549,192 | A | 10/1985 | Hung |
| 2010/0314615 | A1 | 12/2010 | Mizuki et al. |
| 2012/0248973 | A1 | 10/2012 | Ito et al. |

FOREIGN PATENT DOCUMENTS

| CA | 2108669 A1 | 4/1994 |
| EP | 0594538 A2 | 4/1994 |

(Continued)

OTHER PUBLICATIONS

Gritsenko et al., Synthesis of phenothiazines. XXIX. Imidazo[4,5,1-k,1]phenothiazine and its derivatives, 1971, Khimiya Geterotsiklicheskikh Soedinenii 7(6), pp. 767-769.*
Chinese Search Report dated Jun. 8, 2016 in Corresponding Chinese Patent Application No. 201380078156.5.
Extended European Search Report dated Jan. 26, 2017, of the corresponding EP Patent Application No. 13889161.9.
(Continued)

*Primary Examiner* — Gregory D Clark
(74) *Attorney, Agent, or Firm* — Lee & Morse, P.C.

(57) ABSTRACT

A compound represented by Chemical Formula 1, an organic optoelectronic device including the same and a display device including the organic optoelectronic device are disclosed. A structure of the compound represented by Chemical Formula 1 is described in the specification.
The compound provides an organic optoelectronic device having high efficiency, long life-span and the like characteristics.

20 Claims, 1 Drawing Sheet

(51) Int. Cl.
*C07D 471/04* (2006.01)
*C07D 487/04* (2006.01)
*C09K 11/06* (2006.01)
*C07D 471/06* (2006.01)
*C07D 487/06* (2006.01)
*C09K 11/02* (2006.01)
*H01L 27/32* (2006.01)

(52) U.S. Cl.
CPC ......... *C07D 487/04* (2013.01); *C07D 487/06* (2013.01); *C09K 11/025* (2013.01); *C09K 11/06* (2013.01); *H01L 27/3244* (2013.01); *H01L 51/0067* (2013.01); *H01L 51/0074* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0085* (2013.01); *H01L 51/5016* (2013.01)

(56) References Cited

FOREIGN PATENT DOCUMENTS

| | | |
|---|---|---|
| JP | 61-42569 A | 3/1986 |
| JP | 06-192259 A | 7/1994 |
| KR | 10-1994-0009187 A | 5/1994 |
| KR | 10-2009-0010763 A | 1/2009 |
| KR | 10-2010-0136681 A | 12/2010 |
| WO | WO 2009/131254 A1 | 10/2009 |
| WO | WO 2011/126224 A1 | 10/2011 |

OTHER PUBLICATIONS

Reddy, et al., "Novel Imidazophenoxazine-4-Sulfonamides: Their Synthesis and Evaluation as Potential Inhibitors of PDE4" Bioorganic & Medicinal Chemistry, vol. 21, (2013) pp. 1952-1963.
Journal of Medicinal Chemistry, 1990, vol. 33, No. 1, p. 49-52.
Chemistry of Heterocyclic Compounds, Nov. 15, 1973, p. 715-717, Russian Original: Khimiya Geterotsiklicheskikh Soedinenii, 1971, vol. 7, No. 6.

\* cited by examiner

[Fig. 1]
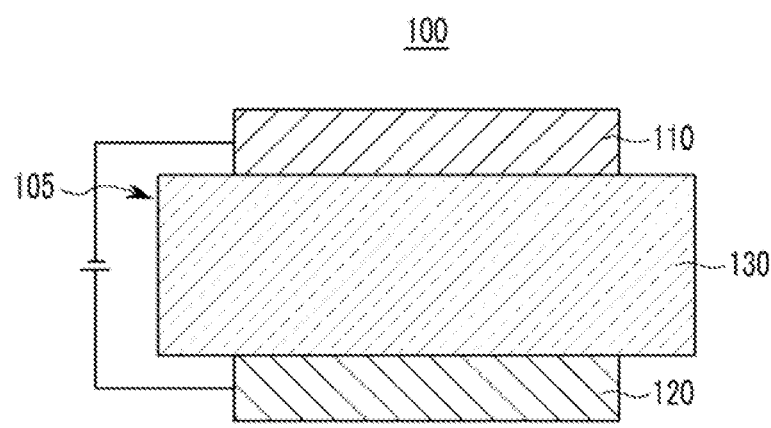
[Fig. 2]
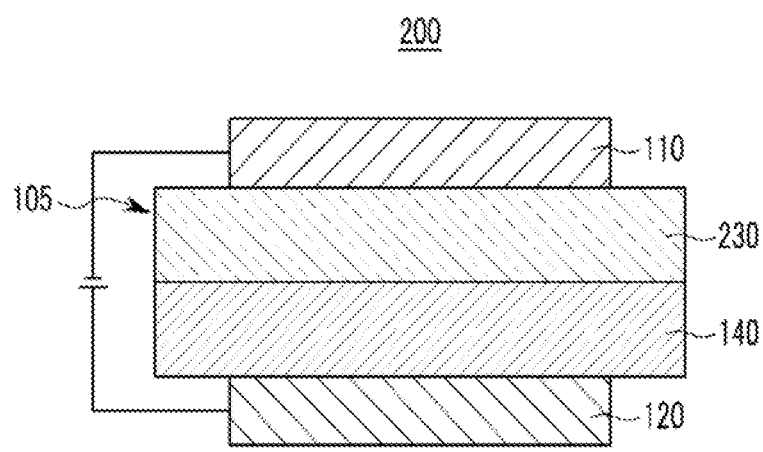

COMPOUND, ORGANIC OPTOELECTRONIC ELEMENT COMPRISING SAME, AND DISPLAY DEVICE

CROSS REFERENCE TO RELATED APPLICATIONS

This is the U.S. national phase application based on PCT Application No. PCT/KR2013/009896, filed Nov. 4, 2013, which is based on Korean Patent Application No. 10-2013-0081722, filed Jul. 11, 2013, the entire contents of all of which are hereby incorporated by reference.

TECHNICAL FIELD

A compound, an organic optoelectronic device including the same and a display device are disclosed.

BACKGROUND ART

An organic optoelectronic device is a device that converts electrical energy into photoenergy, and vice versa.

An organic optoelectronic device may be classified as follows in accordance with its driving principles. One is an optoelectronic device where excitons are generated by photoenergy, separated into electrons and holes the electrons and holes, and are transferred to different electrodes to generate electrical energy, and the other is a light emitting device where a voltage or a current is supplied to an electrode to generate photoenergy from electrical energy.

Examples of an organic optoelectronic device may be an organic photoelectric device, an organic light emitting diode, an organic solar cell and an organic photo conductor drum.

Of these, an organic light emitting diode (OLED) has recently drawn attention due to an increase in demand for flat panel displays. Such an organic light emitting diode converts electrical energy into light by applying current to an organic light emitting material. It has a structure in which an organic layer is interposed between an anode and a cathode. Herein, an organic layer may include an emission layer and optionally an auxiliary layer, and the auxiliary layer may include, for example at least one selected from a hole injection layer, a hole transport layer, an electron blocking layer, an electron transport layer, an electron injection layer, and a hole blocking layer in order increase efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

One embodiment provides a compound being capable of realizing an organic optoelectronic device having high efficiency and long life-span.

An organic optoelectronic device including the compound and a display device including the organic optoelectronic device are provided.

Technical Solution

In one embodiment of the present invention, a compound represented by Chemical Formula 1 provided.

[Chemical Formula 1]

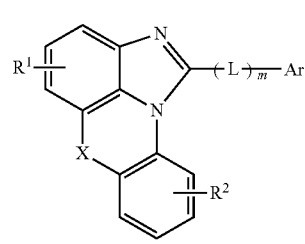

In Chemical Formula 1, L is a substituted or unsubstituted C6 to C30 arylene group, or a substituted or unsubstituted C2 to C30 heteroarylene group, m is an integer ranging from 0 to 3, Ar is a substituted or unsubstituted C6 to C30 aryl group or a substituted or unsubstituted C2 to C30 heteroaryl group, and X is O, S, SO$_2$(O=S=O), PO(P=O), NR', CR'R" or SiR'R", the R' and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and R$^1$ and R$^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

In another embodiment of the present invention, an organic optoelectronic device includes an anode and a cathode facing each other; and at least one organic layer between the anode and the cathode, wherein the organic layer includes the compound according to one embodiment of the present invention.

In yet another embodiment of the present invention, a display device including the organic optoelectronic device according to one embodiment of the present invention is provided.

Advantageous Effects

An organic optoelectronic device having high efficiency and long life-span may be realized.

DESCRIPTION OF THE DRAWINGS

FIGS. 1 and 2 are cross-sectional views showing organic light emitting diodes according to various embodiments.

<Description of Reference Numerals Indicating Primary Elements in the Drawings>

100: organic light emitting diode 200: organic light emitting diode
105: organic layer
110: cathode
120: anode
130: emission layer 230: emission layer
140: hole auxiliary layer

MODE FOR INVENTION

Hereinafter, embodiments of the present invention are described in detail. However, these embodiments are exemplary, and this disclosure is not limited thereto.

In the present specification, when a definition is not otherwise provided, the term "substituted" refers to one substituted with a substituent selected from deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of a substituent or a compound.

In addition, the adjacent two substituents selected from the substituted halogen, hydroxyl group, amino group, substituted or unsubstituted C1 to C20 amine group, a nitro group, a substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as a trifluoromethyl group and the like, or cyano group may be fused to each other to form a ring. Specifically, the substituted C6 to C30 aryl group may be fused to another adjacent substituted C6 to C30 aryl group to form a substituted or unsubstituted fluorene ring.

In the present specification, when specific definition is not otherwise provided, "hetero" refers to one including 1 to 3 hetero atoms selected from N, O, S, and P, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C20 alkyl group. More specifically, the alkyl group may be a C1 to C6 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, the term "aryl group" refers to a substituent including all element of the cycle having p-orbitals which form conjugation, and may be monocyclic, or fused ring polycyclic (i.e., rings sharing adjacent pairs of carbon atoms) functional group.

In the present specification, the term "heteroaryl group" refers to aryl group including 1 to 3 heteroatoms selected from N, O, S, and P and remaining carbon. When the heteroaryl group is a fused ring, each ring may include 1 to 3 heteroatoms.

More specifically, a substituted or unsubstituted C6 to C30 aryl group and/or a substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted carbazolyl group, a substituted or unsubstituted dibenzofuranyl group, a substituted or unsubstituted dibenzothiophenyl group, or a combination thereof, but is not limited thereto.

For specific examples, the substituted or unsubstituted fluorenyl group included in the substituted C6 to C30 aryl group may be Chemical Formula 30 or Chemical Formula 31.

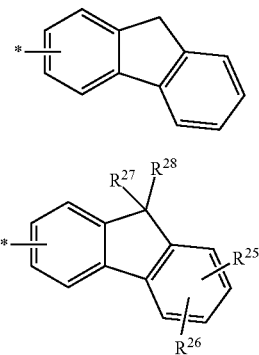

[Chemical Formula 30]

[Chemical Formula 31]

In Chemical Formula 30 and Chemical Formula 31, $R^{25}$ to $R^{28}$ are independently hydrogen, deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, and * indicates a position linking to an carbon atom or an atom except carbon.

In the present specification, hole characteristics refer to characteristics that holes formed in the anode is easily injected into the emission layer and transported in the emission layer due to conductive characteristics according to HOMO level. More specifically, it is similar to electron-repelling characteristics.

Electron characteristics refer to characteristics that electron formed in the cathode is easily injected into the emission layer and transported in the emission layer due to conductive characteristics according to LUMO level. More specifically, it is similar to electron-withdrawing characteristics.

In one embodiment of the present invention, a compound represented by Chemical Formula 1 is provided.

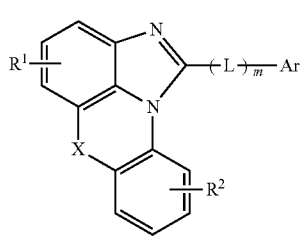

[Chemical Formula 1]

In Chemical Formula 1, L is a substituted or unsubstituted C6 to C30 arylene group, or a substituted or unsubstituted C2 to C30 heteroarylene group, m is an integer ranging from 0 to 3, Ar is a substituted or unsubstituted C6 to C30 aryl group or a substituted or unsubstituted C2 to C30 heteroaryl group, X is O, S, $SO_2(O=S=O)$, $PO(P=O)$, NR', CR'R" or SiR'R", the R' and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $R^1$ and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

The compound according to one embodiment of the present invention has hole characteristics and electron characteristics simultaneously and transports holes and electrons effectively.

The compound represented by Chemical Formula 1 may have various energy bandgaps by various substituents.

When the compound having an appropriate energy level depending on a substituent is used to manufacture an organic optoelectronic device, the compound reinforces hole transport capability or electron transport capability and thus, brings about excellent effects in terms of efficiency and a driving voltage, and also, has excellent electrochemical and thermal stability and thus, may improve life-span characteristics of the organic optoelectronic device.

Specifically, $R^1$ may be hydrogen, deuterium, a substituted or unsubstituted C1 to C20 alkyl group, or a substituted or unsubstituted C3 to C40 silyl group, and the Ar is a substituted or unsubstituted C6 to C30 aryl group, or a substituted or unsubstituted C2 to C30 heteroaryl group having electron characteristics.

When $R^1$ and Ar are represented as above, hole and electron characteristics may further improved.

More specifically, Ar may be a compound represented by one of Chemical Formulae ET-1 to ET-35.

[Chemical Formula ET-1]

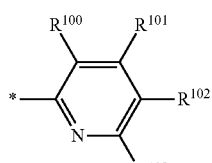

[Chemical Formula ET-2]

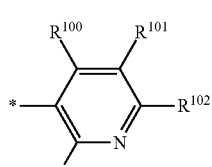

[Chemical Formula ET-3]

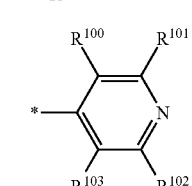

[Chemical Formula ET-4]

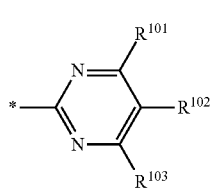

[Chemical Formula ET-5]

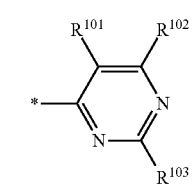

[Chemical Formula ET-6]

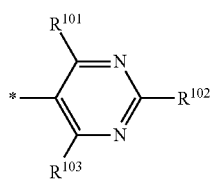

[Chemical Formula ET-7]

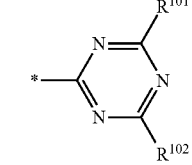

In Chemical Formulae ET-1 to ET-7, * indicates a position where it is linked to carbon (C) or an element except carbon, and the $R^{100}$ to $R^{110}$ may independently be hydrogen, deuterium, a substituted or unsubstituted C1 to C30 alkyl group, a substituted or unsubstituted C6 to C30 aryl group, or a substituted or unsubstituted C2 to C30 heteroaryl group.

In Chemical Formula 1, the X may be NR' or CR'R", and the R' and R" may independently be hydrogen, deuterium, a substituted or unsubstituted C1 to C20 alkyl group, a substituted or unsubstituted C6 to C30 aryl group, or a substituted or unsubstituted C2 to C30 heteroaryl group, and the R' may be a compound represented by Chemical Formula X-1.

[Chemical Formula X-1]

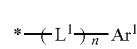

In Chemical Formula X-1, * indicates a position where it is linked to nitrogen (N), $L^1$ is a substituted or unsubstituted C6 to C30 arylene group, or a substituted or unsubstituted C2 to C30 heteroarylene group, n is an integer ranging from 0 to 3, and Ar' is a substituted or unsubstituted C6 to C30 aryl group or a substituted or unsubstituted C2 to C30 heteroaryl group.

Specifically, Chemical Formula X-1 may be a compound represented by Chemical Formula X-2 or Chemical Formula X-3:

[Chemical Formula X-2]

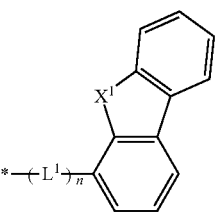

[Chemical Formula X-3]

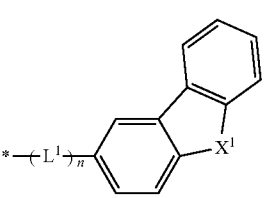

In Chemical Formulae X-2 or X-3, * indicates a position where it is linked to nitrogen (N), $L^1$ is a substituted or unsubstituted C6 to C30 arylene group, or a substituted or unsubstituted C2 to C30 heteroarylene group, n is an integer ranging from 0 to 3, $X^1$ is NR', O or S, wherein R' are independently hydrogen, deuterium, a substituted or unsubstituted C1 to C20 alkyl group, a substituted or unsubstituted C6 to C30 aryl group, or a substituted or unsubstituted C2 to C30 heteroaryl group.

In Chemical Formula 1, the $R^1$ may be hydrogen, deuterium, a substituted or unsubstituted C1 to C10 alkyl group, or a substituted or unsubstituted silyl group, and the $R^2$ may be hydrogen, deuterium, a substituted or unsubstituted C1 to C20 alkyl group, a substituted or unsubstituted C6 to C30 aryl group, or a substituted or unsubstituted C2 to C30 heteroaryl group. Herein, the substituted or unsubstituted C6 to C30 aryl group may be a substituted or unsubstituted phenyl group, a substituted or unsubstituted naphthyl group, a substituted or unsubstituted biphenyl group, a substituted or unsubstituted anthracenyl group, a substituted or unsubstituted phenanthryl group, or a substituted or unsubstituted triphenylenyl group.

The substituted or unsubstituted C2 to C30 heteroaryl group may be a compound represented by one of Chemical Formula X-4 to Chemical Formula X-6.

[Chemical Formula X-4]

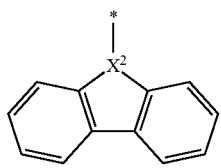

[Chemical Formula X-5]

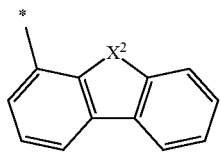

[Chemical Formula X-6]

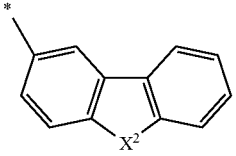

In Chemical Formulae X-4 to X-6,
* indicates a position where it is linked to the carbon (C),
in Chemical Formula X-4, $X^2$ is N, and
in Chemical Formulae X-5 and X-6, $X^2$ is NR', O or S, wherein R' is hydrogen, deuterium, a substituted or unsubstituted C1 to C20 alkyl group, a substituted or unsubstituted C6 to C30 aryl group, or a substituted or unsubstituted C2 to C30 heteroaryl group.

The substituted or unsubstituted C2 to C30 heteroaryl group may be a compound represented by Chemical Formula X-7.

[Chemical Formula X-7]

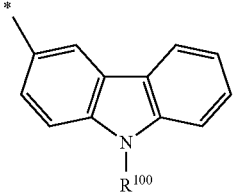

In Chemical Formula X-7, * indicates a position where it is linked to the carbon (C), and $R^{100}$ is a substituted or unsubstituted C1 to C30 alkyl group, or a substituted or unsubstituted C6 to C30 aryl group.

When X is as above, hole characteristics increase.

In addition, the L may be selectively adjusted to determine conjugation length of the compound, and thus, a triplet energy bandgap may be adjusted based on the adjustment of the L. Accordingly, characteristics of a material required in an organic optoelectronic device may be realized. The triplet energy bandgap may be adjusted by changing bonding position of ortho, para, and meta.

Specific examples of the L may be a substituted or unsubstituted phenylene group, a substituted or unsubstituted biphenylene group, a substituted or unsubstituted p-terphenylene group, a substituted or unsubstituted m-terphenylene group, a substituted or unsubstituted o-terphenylene group, a substituted or unsubstituted naphthylene group, a substituted or unsubstituted anthracenylene group, a substituted or unsubstituted phenanthrylene group, a substituted or unsubstituted pyrenylene group, or a substituted or unsubstituted fluorenylene group, and the like.

More specifically, the substituted or unsubstituted phenylene group may be Chemical Formulae S-1, S-2 and S-3.

[Chemical Formula S-1]

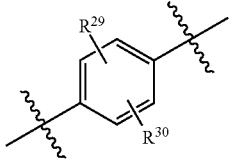

[Chemical Formula S-2]

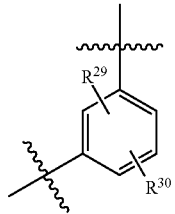

[Chemical Formula S-3]

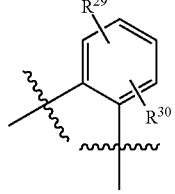

More specifically, the substituted or unsubstituted biphenylene group may be Chemical Formulae S-4, S-5 and S-6.

[Chemical Formula S-4]

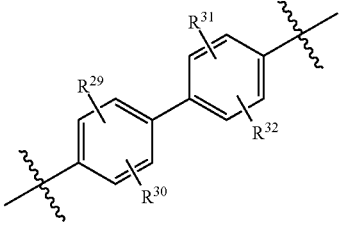

[Chemical Formula S-5]

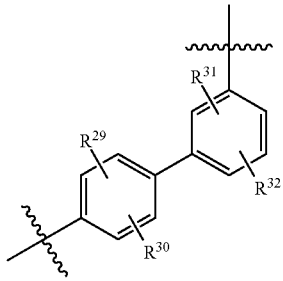

[Chemical Formula S-6]
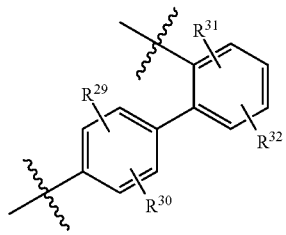
Specific examples of compounds according to one embodiment are as follows, but are not limited thereto.
[A-1]
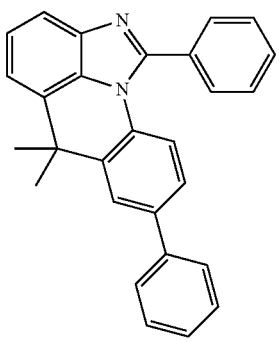
[A-2]
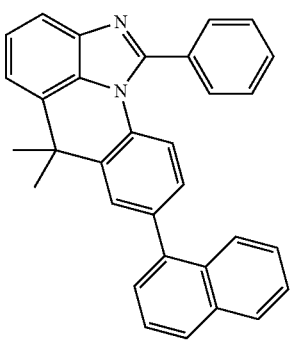
[A-3]
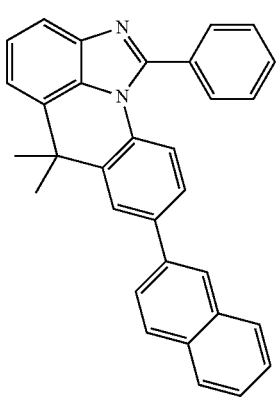
[A-4]
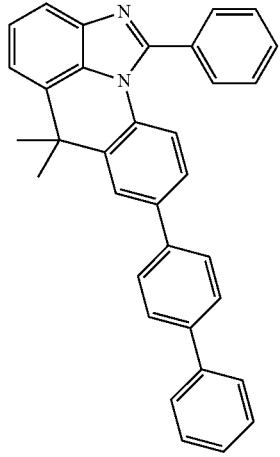
[A-5]
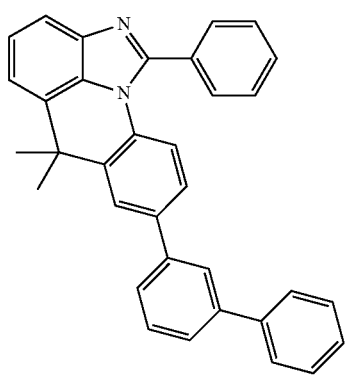
[A-6]
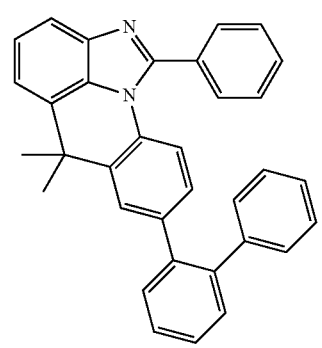
[A-7]
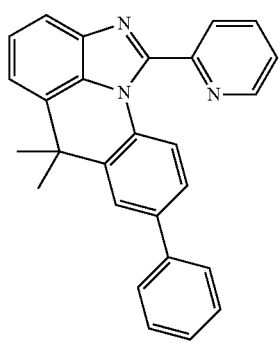

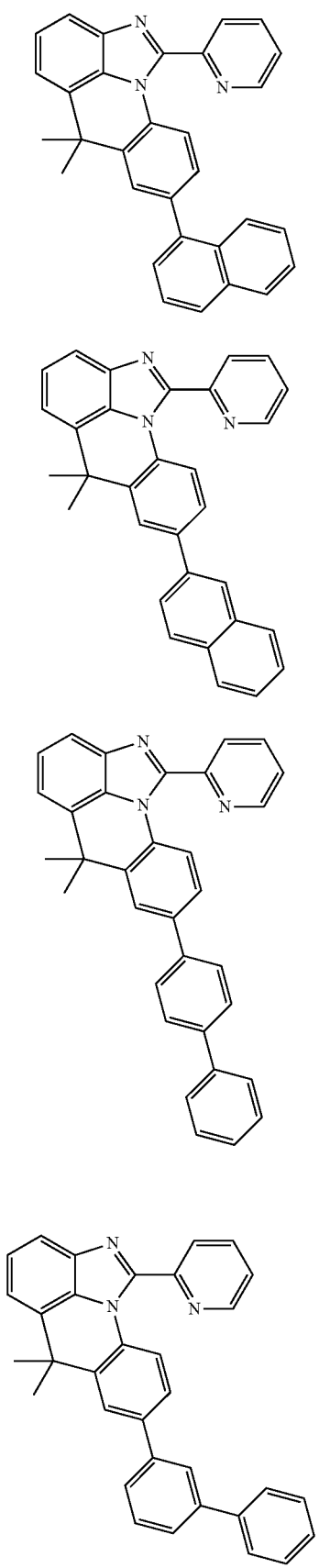
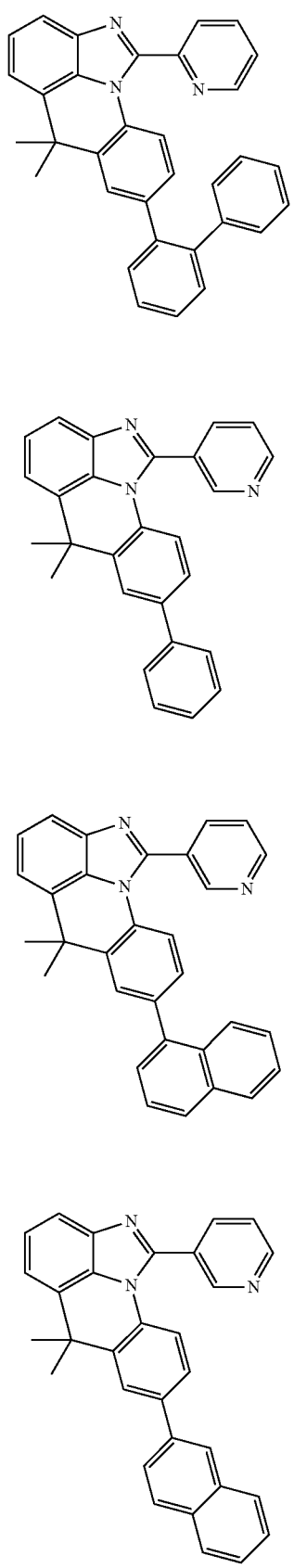

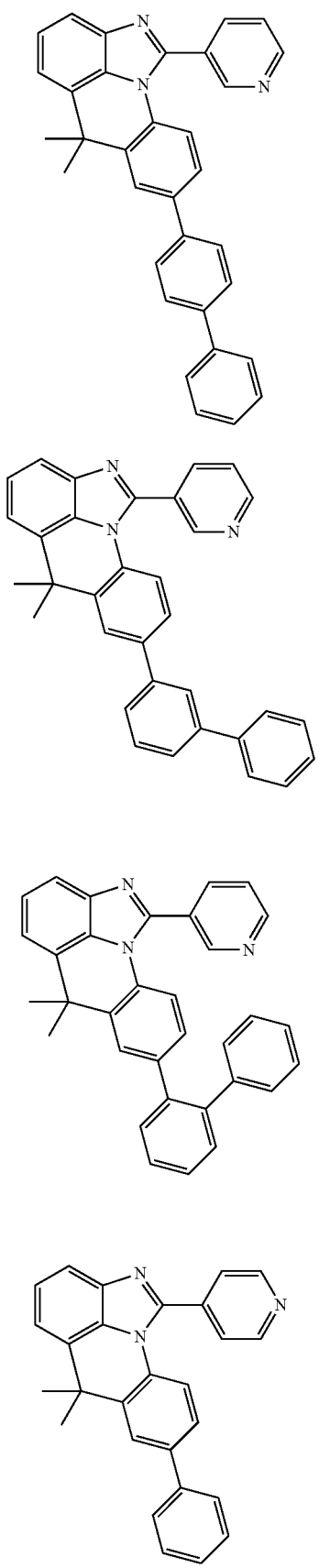
[A-16]
[A-17]
[A-18]
[A-19]
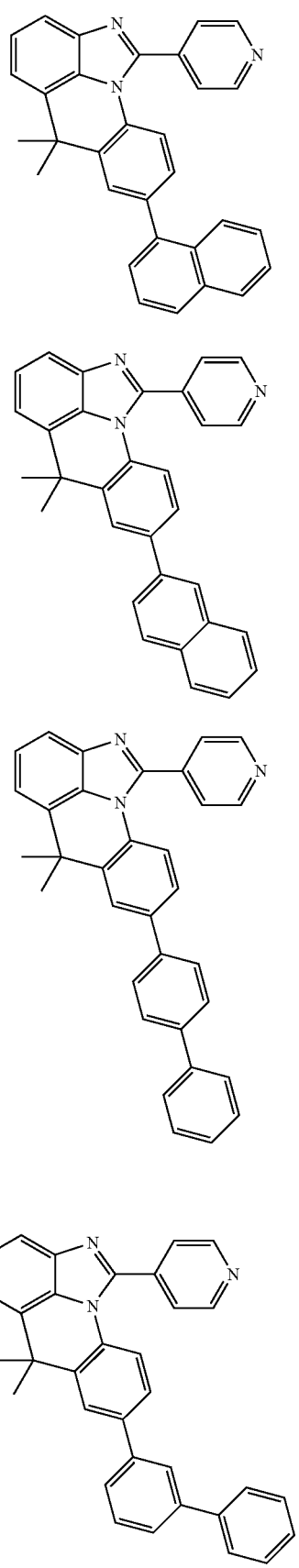
[A-20]
[A-21]
[A-22]
[A-23]

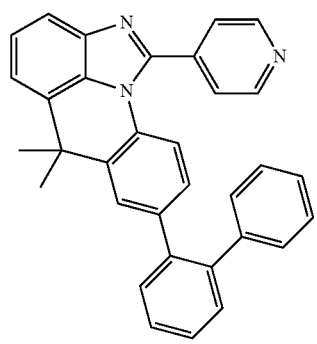
[A-24]
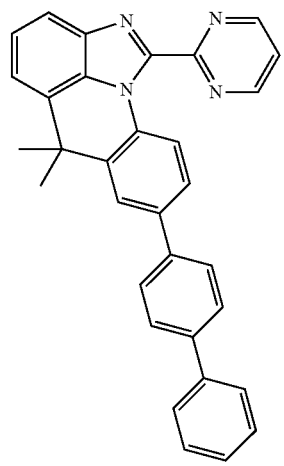
[A-28]
[A-25]
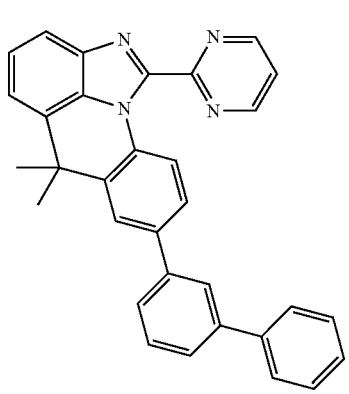
[A-29]
[A-26]
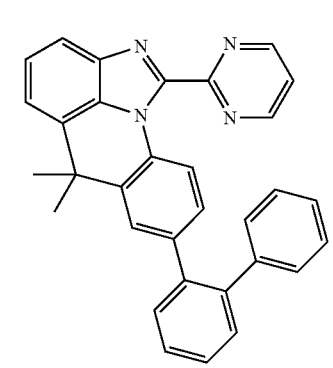
[A-30]
[A-27]
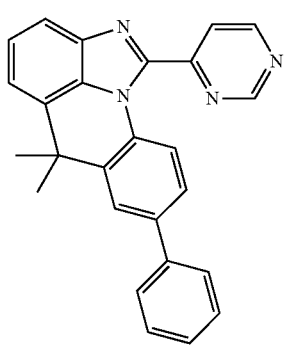
[A-31]

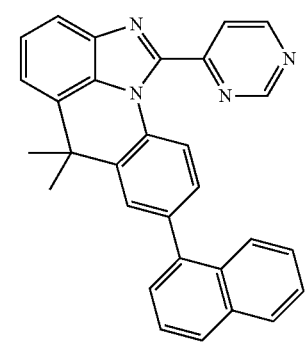
[A-32]
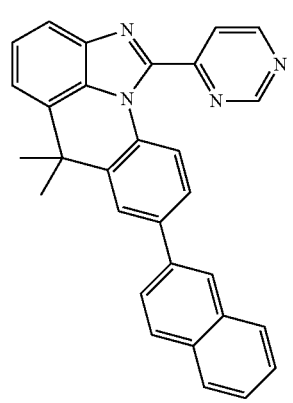
[A-33]
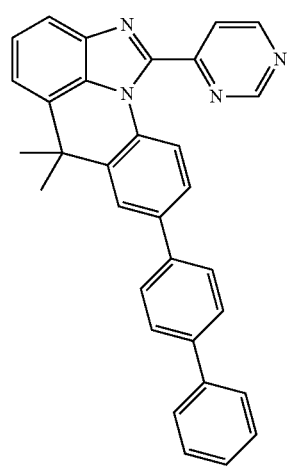
[A-34]
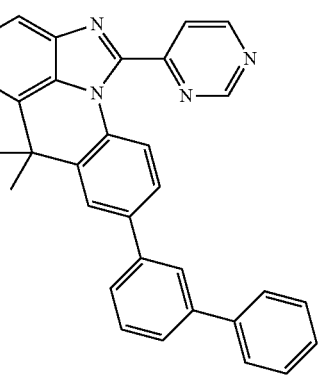
[A-35]
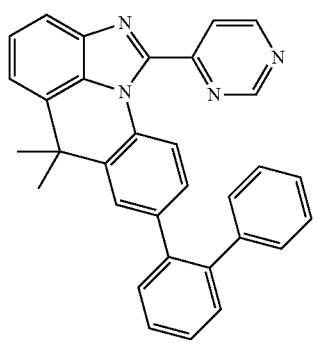
[A-36]
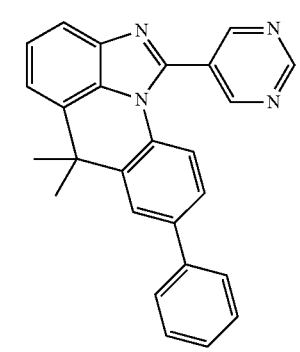
[A-37]
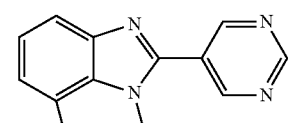
[A-38]
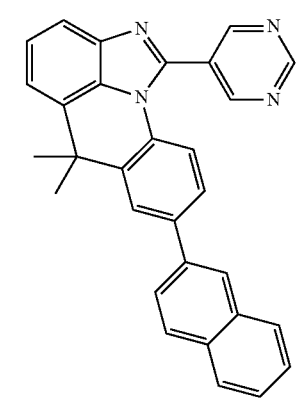
[A-39]

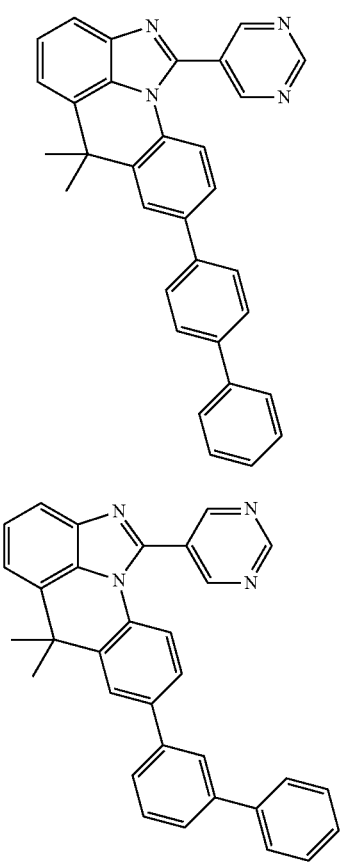
[A-40]
[A-41]
[A-42]
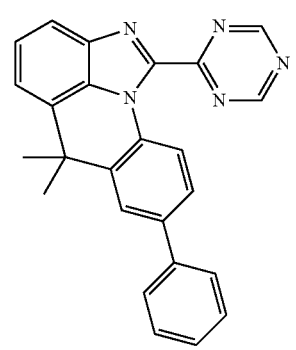
[A-43]
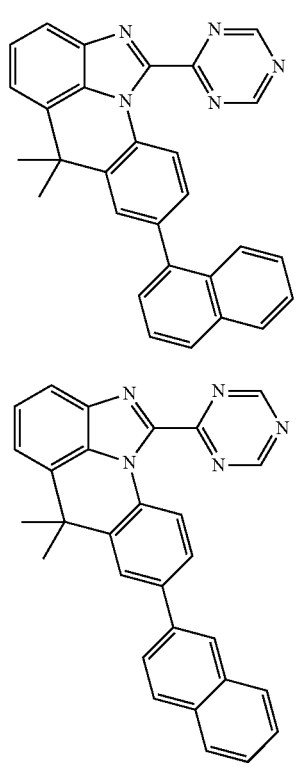
[A-44]
[A-45]
[A-46]
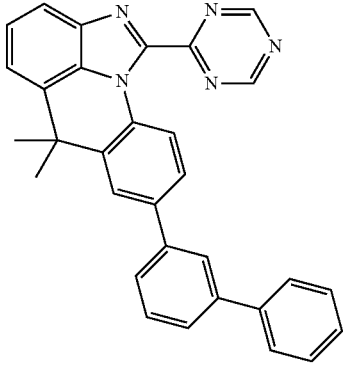
[A-47]

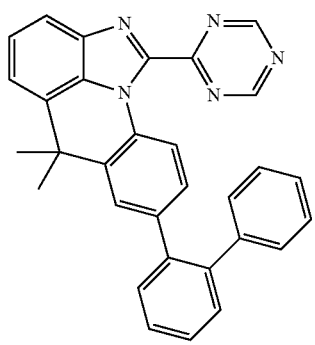
[A-48]
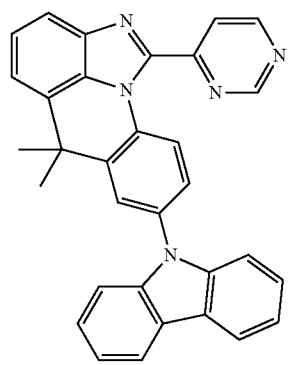
[A-52]
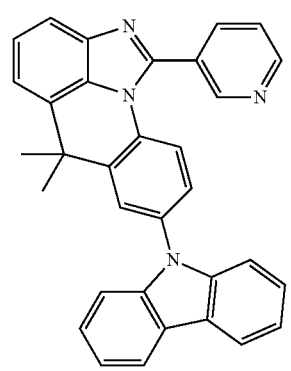
[A-49]
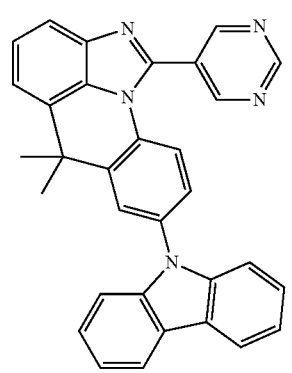
[A-53]
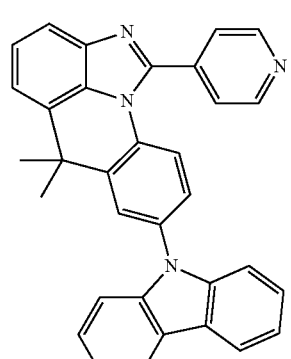
[A-50]
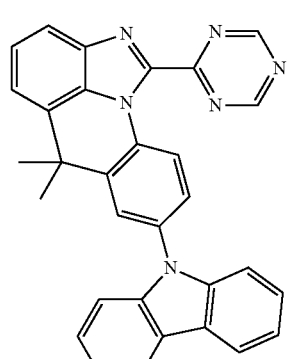
[A-54]
[A-51]
[A-55]

[A-56]
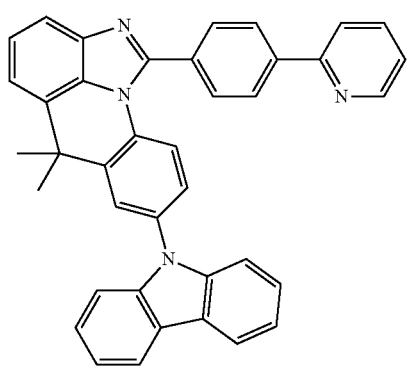
[A-57]
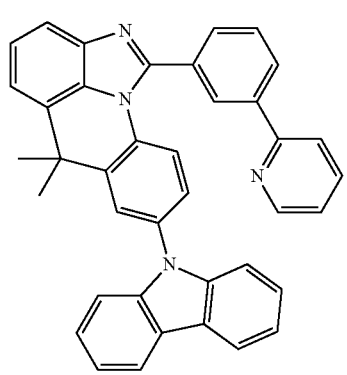
[A-58]
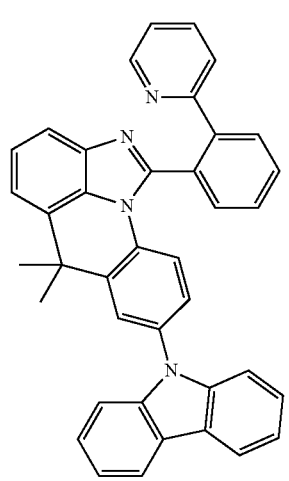
[A-59]
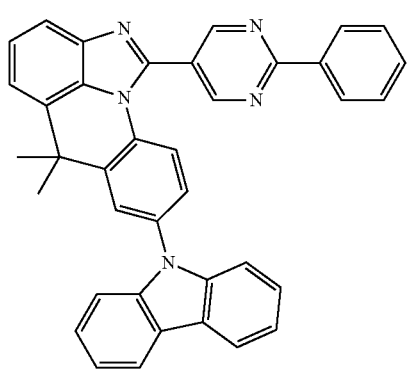
[A-60]
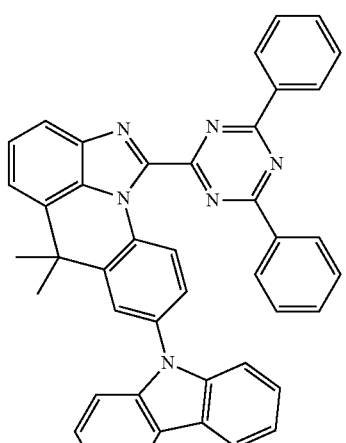
[A-61]
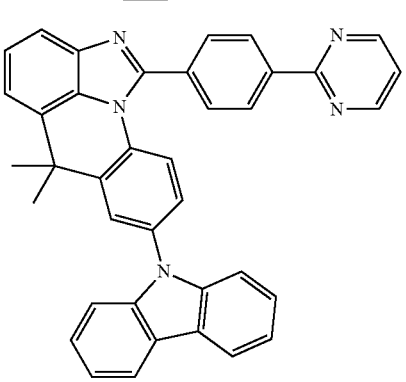
[A-62]
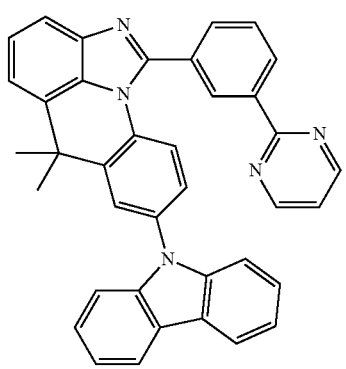
[A-63]
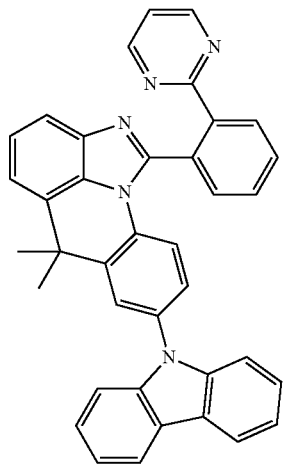

[A-64]
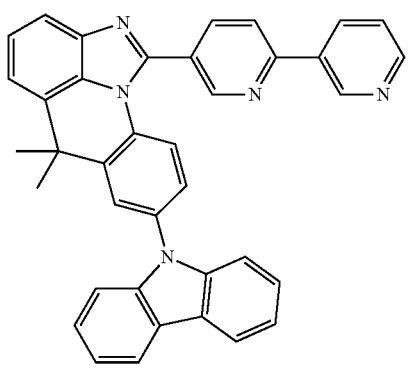
[A-65]
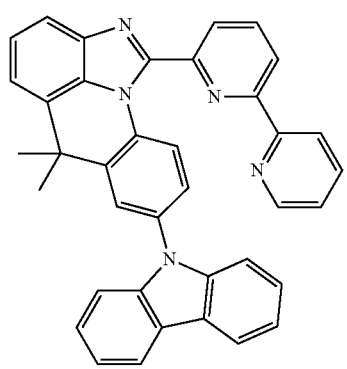
[A-66]
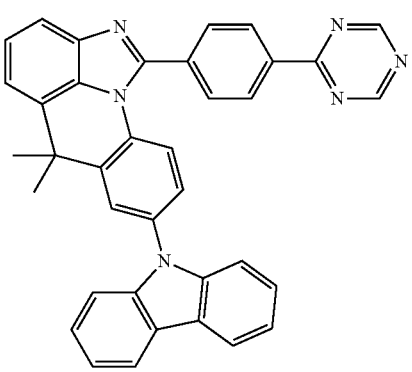
[A-67]
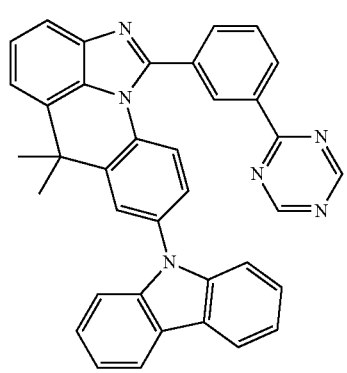
[A-68]
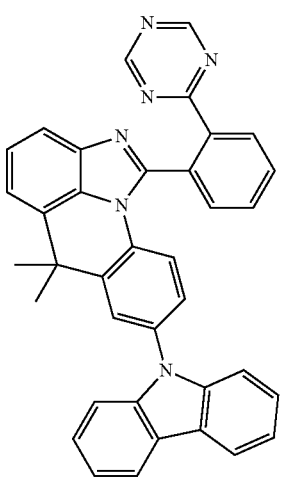
[A-69]
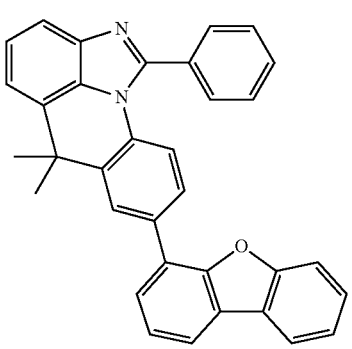
[A-70]
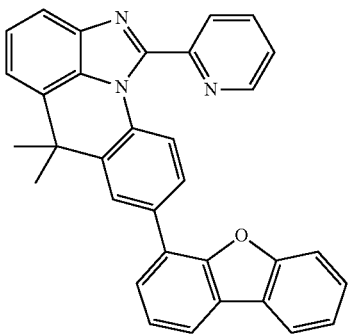
[A-71]
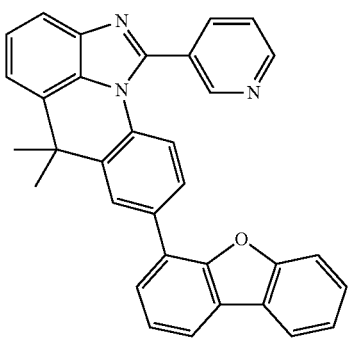

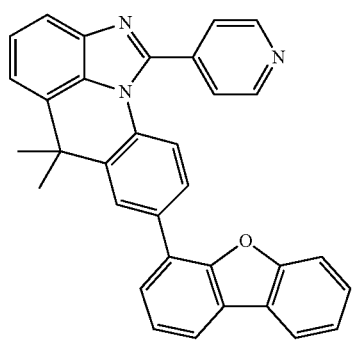
[A-72]
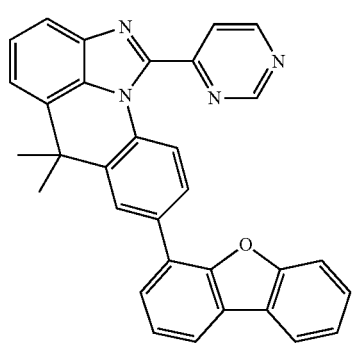
[A-73]
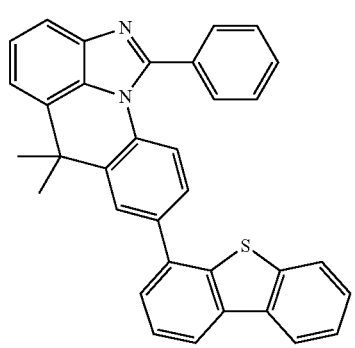
[A-74]
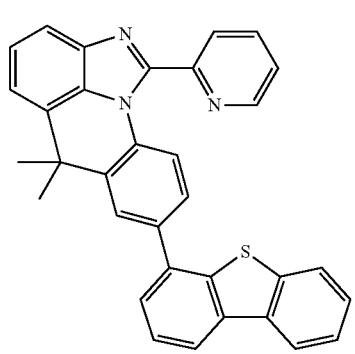
[A-75]
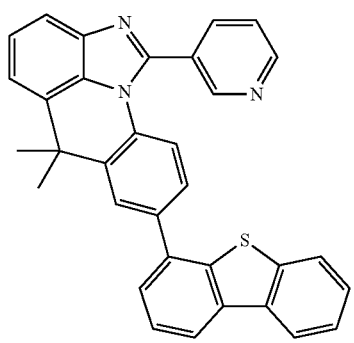
[A-76]
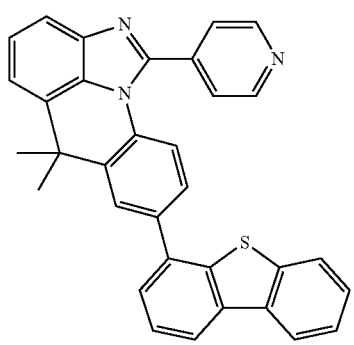
[A-77]
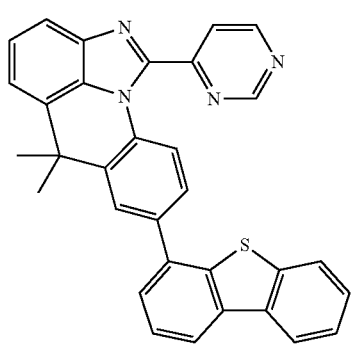
[A-78]
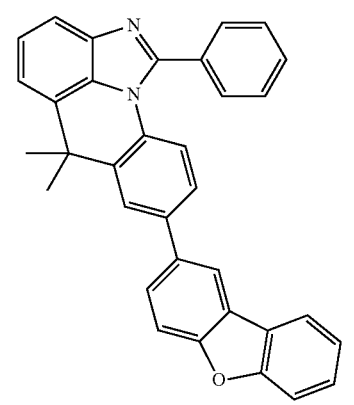
[A-79]

[A-80]
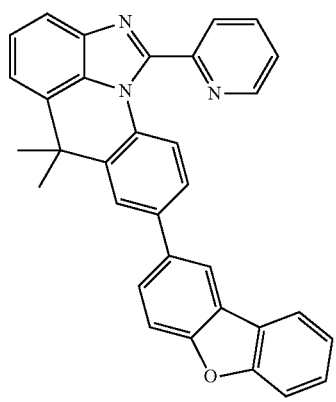
[A-81]
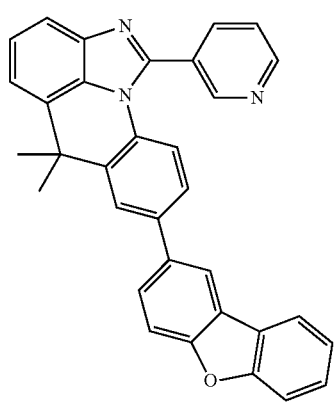
[A-82]
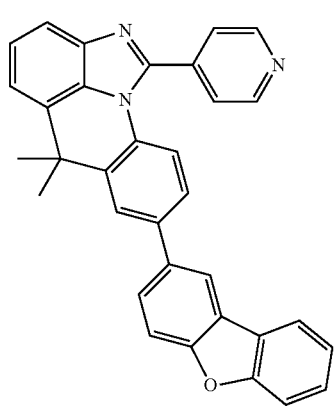
[A-83]
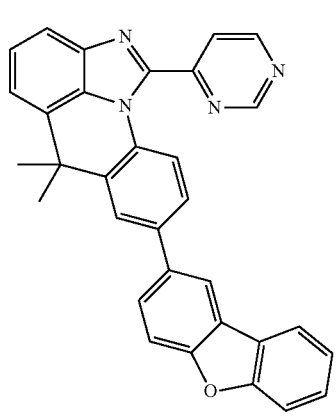
[A-84]
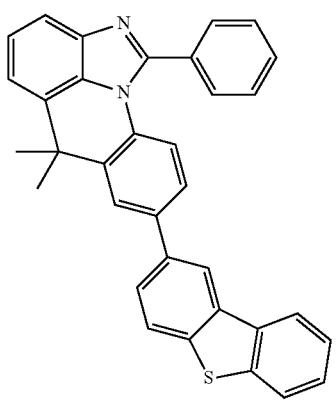
[A-85]
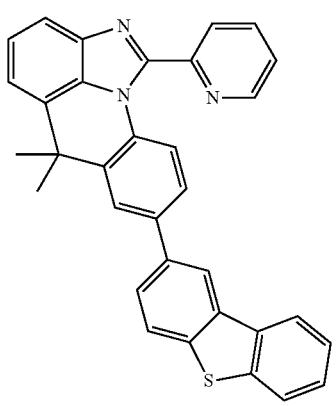
[A-86]
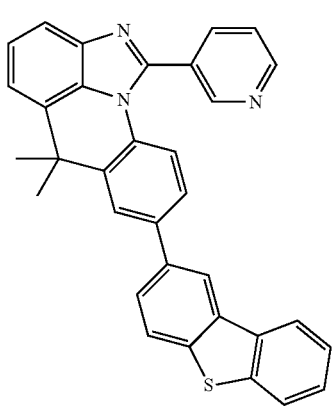
[A-87]
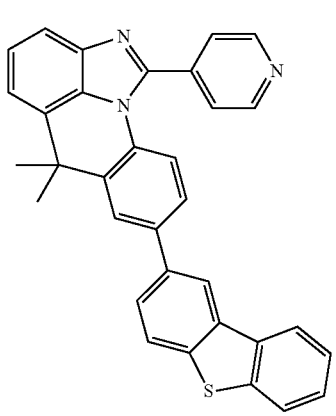

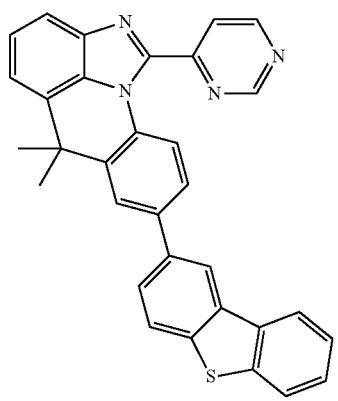 [A-88]
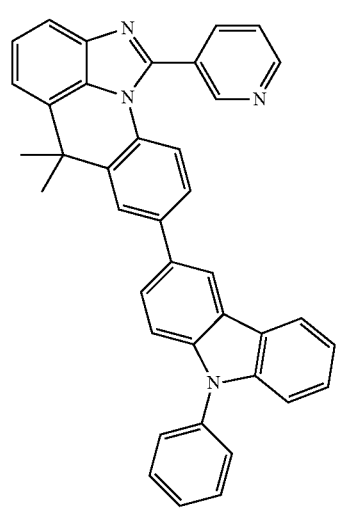 [A-91]
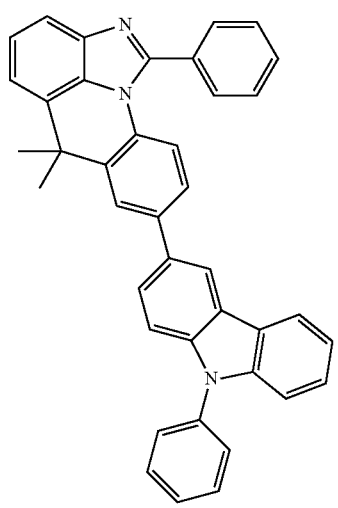 [A-89]
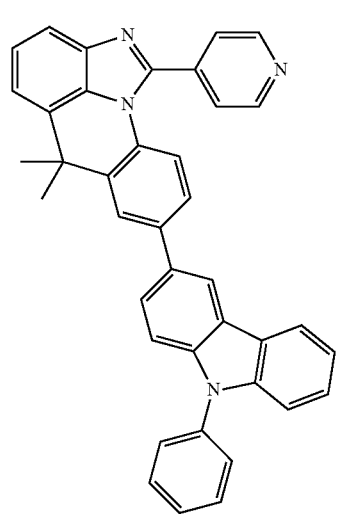 [A-92]
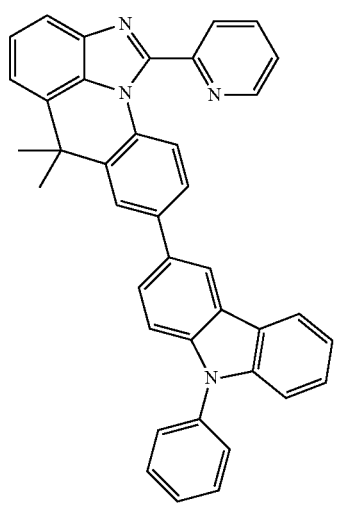 [A-90]
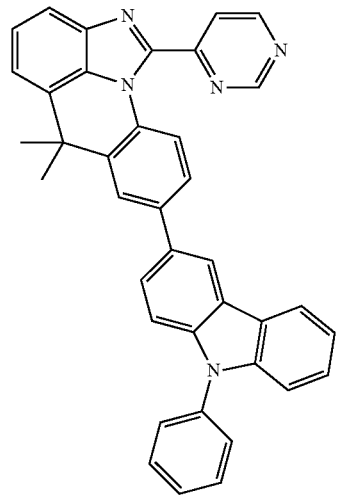 [A-93]

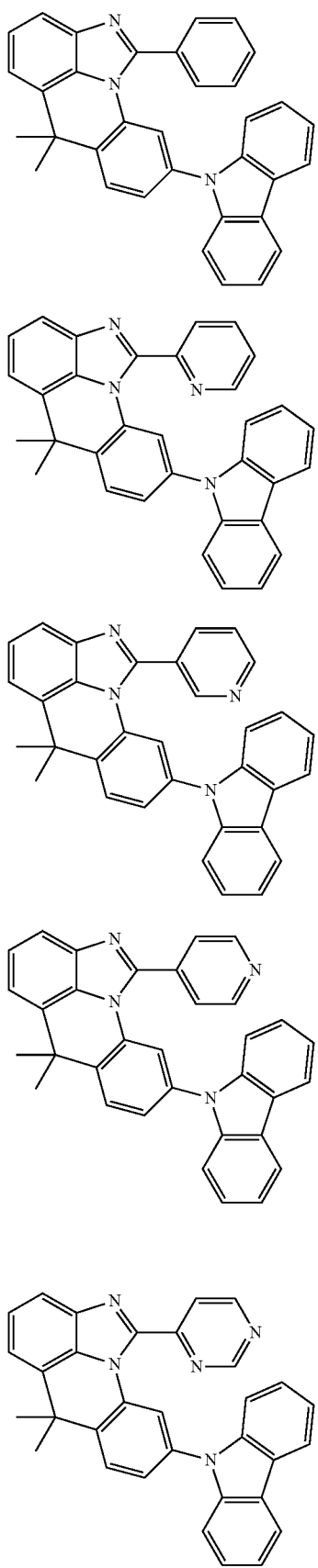
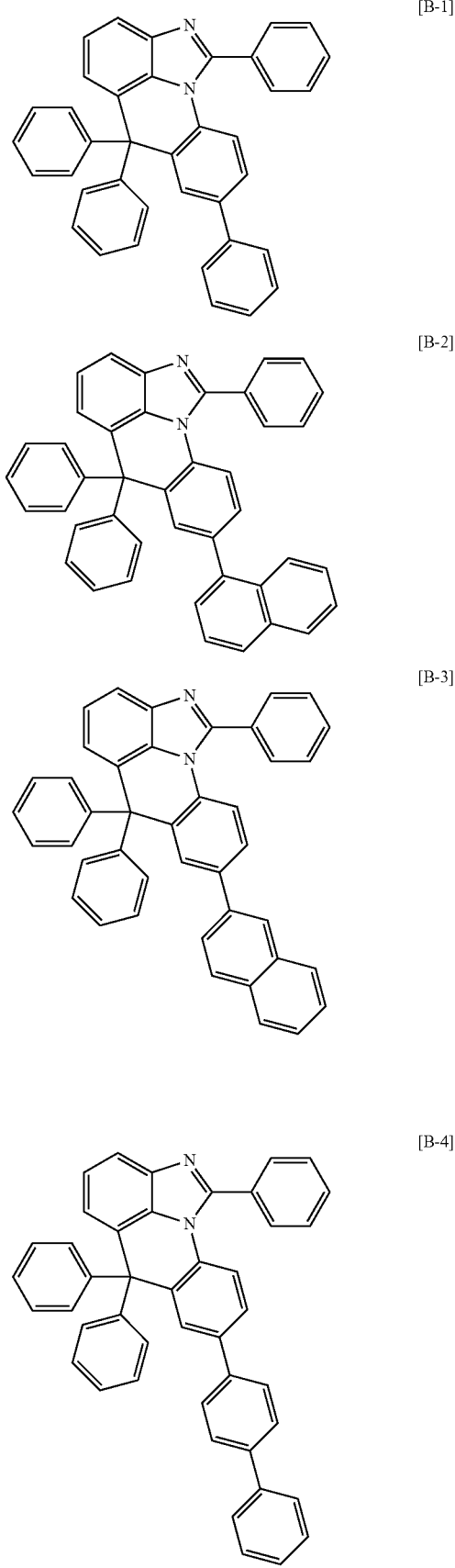

-continued
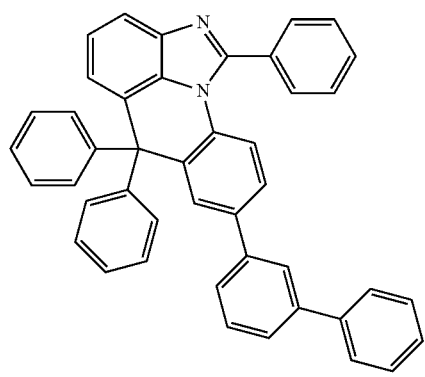
[B-5]
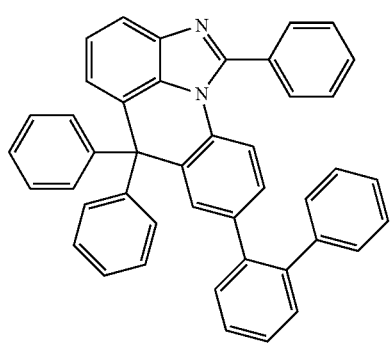
[B-6]
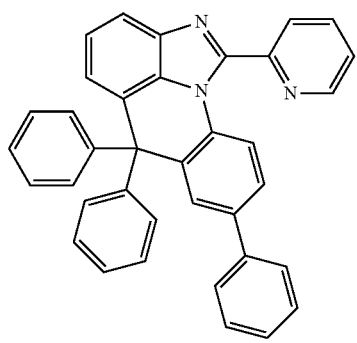
[B-7]
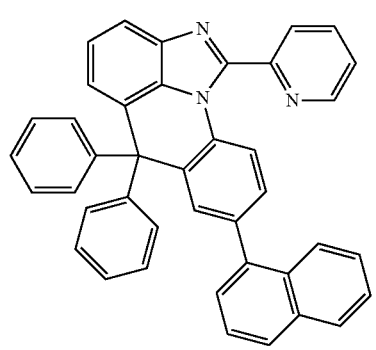
[B-8]
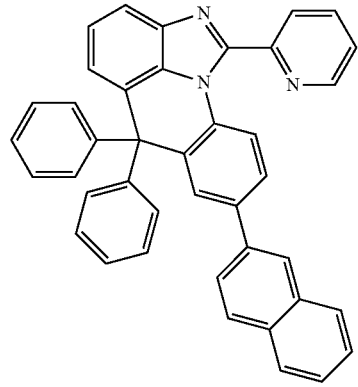
[B-9]
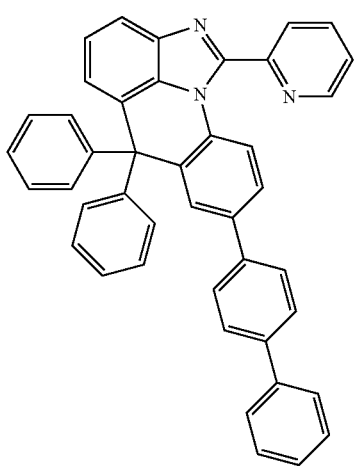
[B-10]
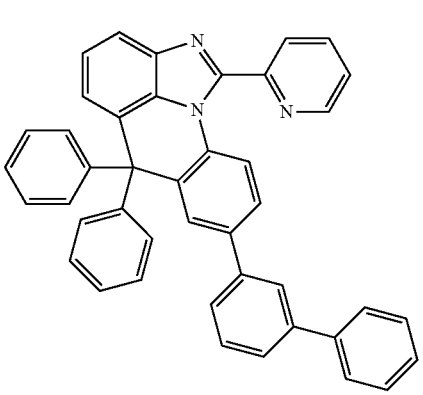
[B-11]
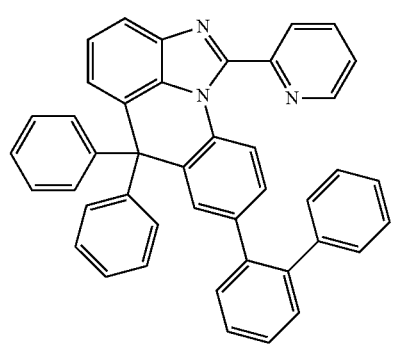
[B-12]

[B-13]
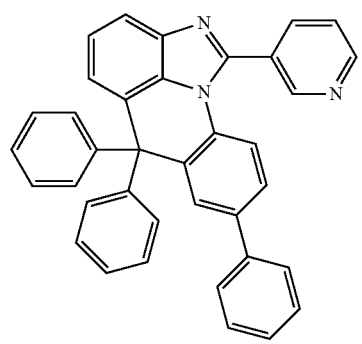
[B-14]
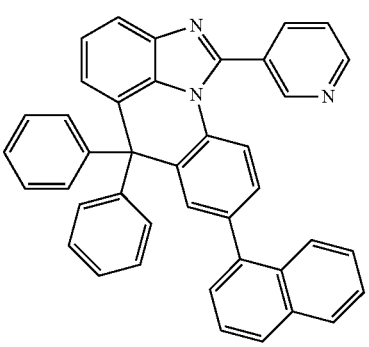
[B-15]
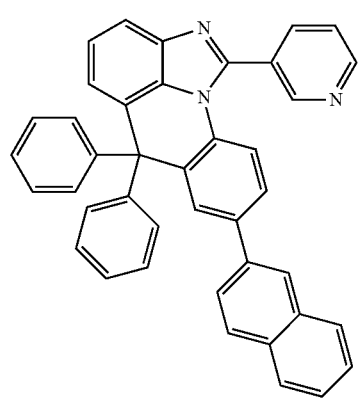
[B-16]
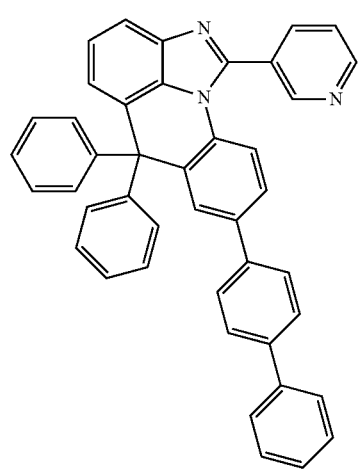
[B-17]
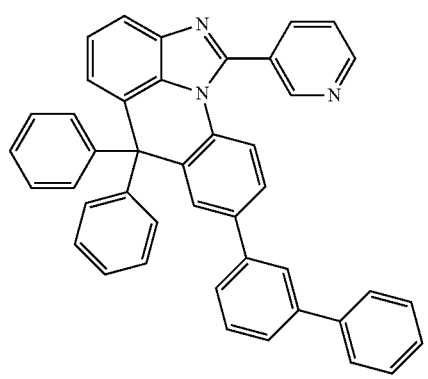
[B-18]
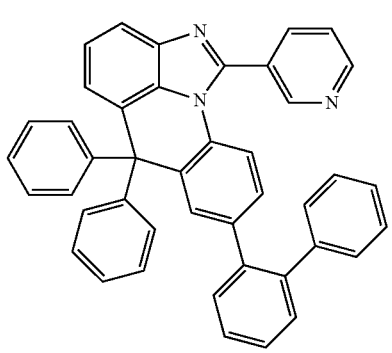
[B-19]
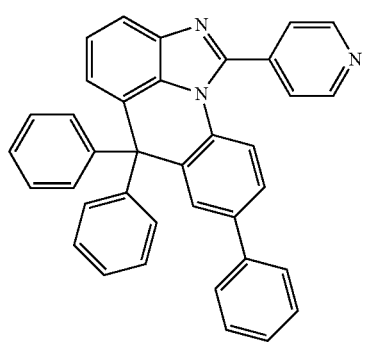
[B-20]
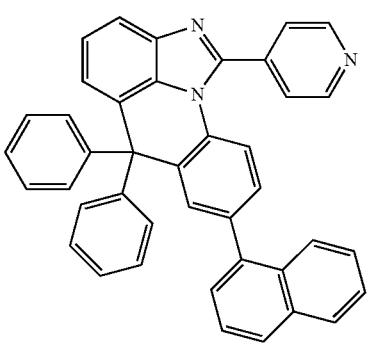

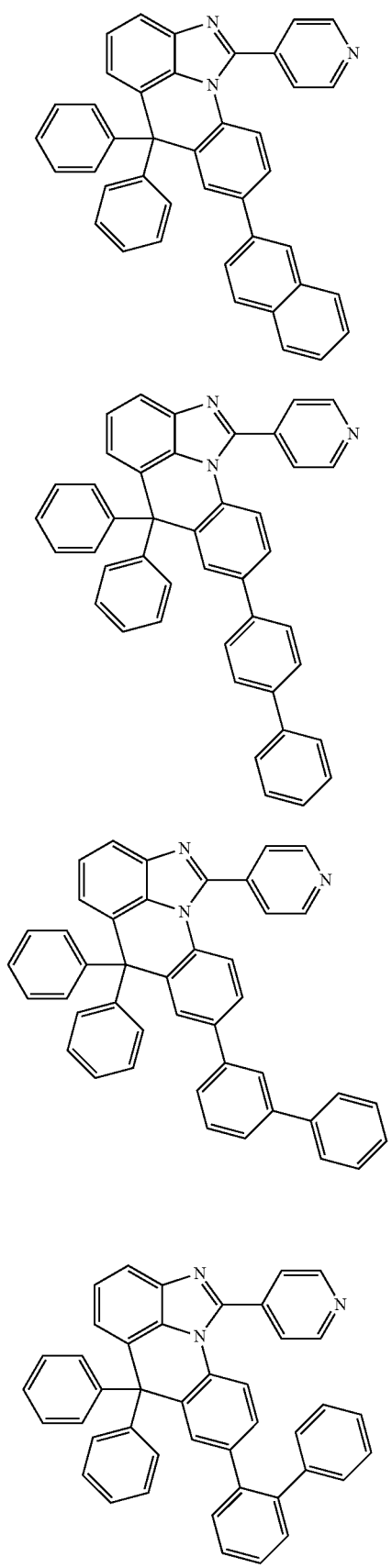
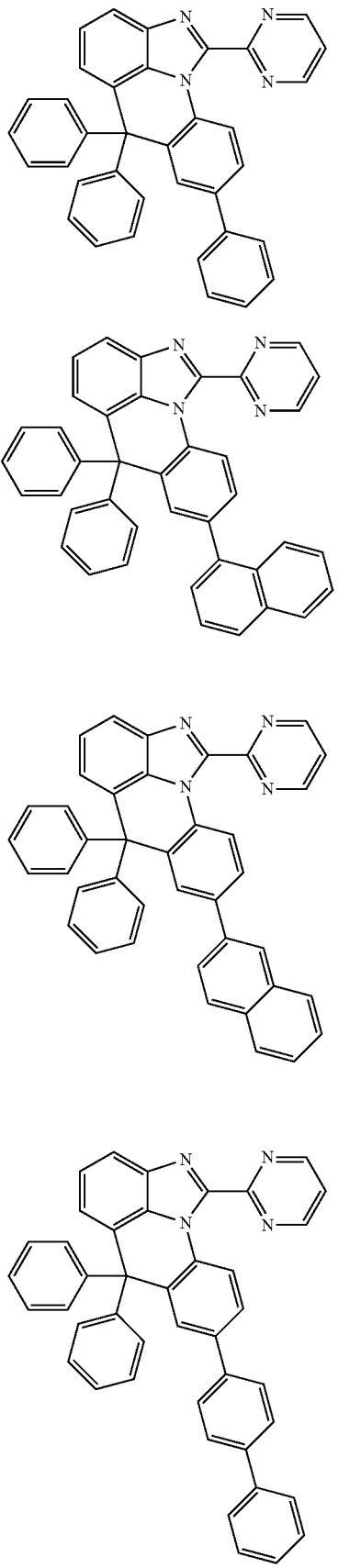

[B-29]
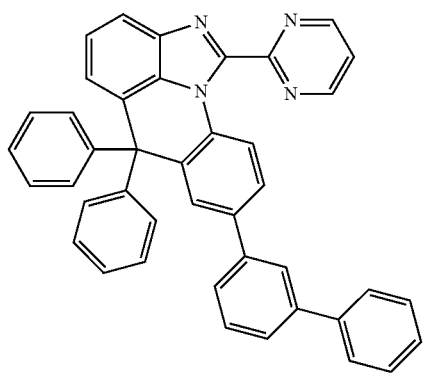
[B-30]
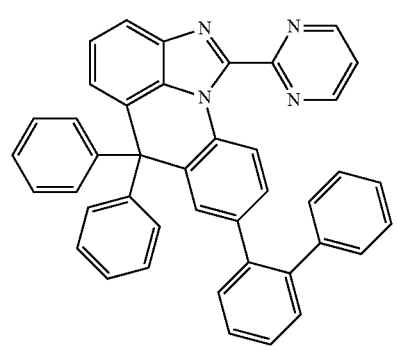
[B-31]
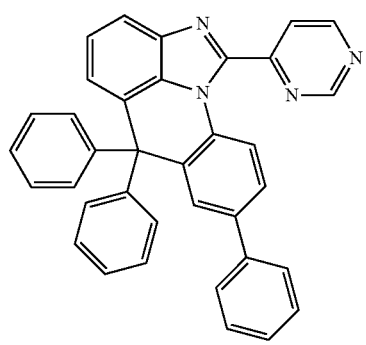
[B-32]
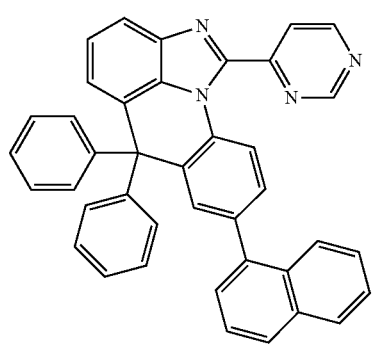
[B-33]
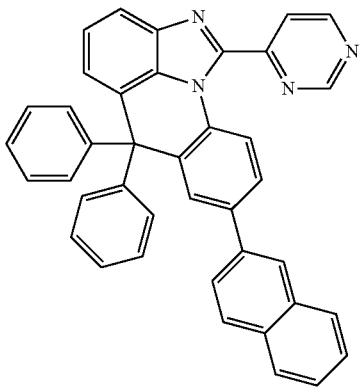
[B-34]
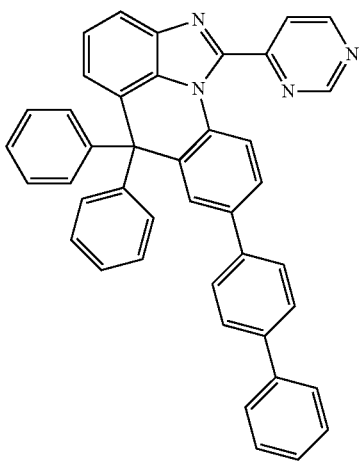
[B-35]
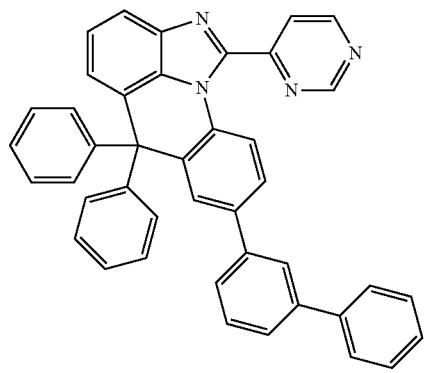
[B-36]
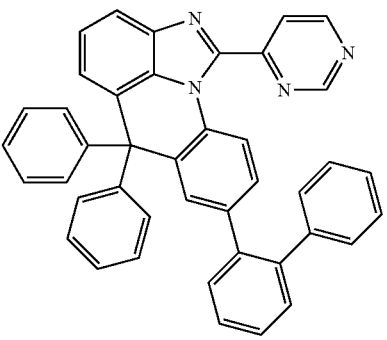

-continued
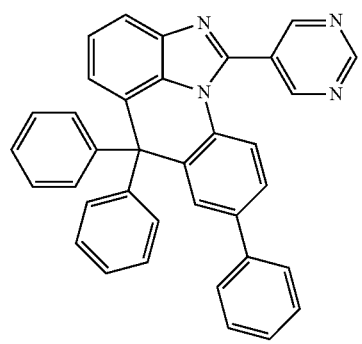
[B-37]
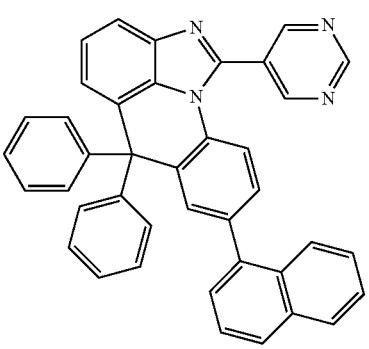
[B-38]
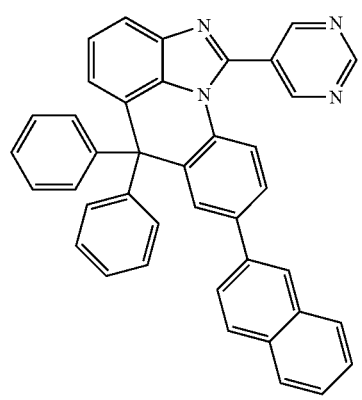
[B-39]
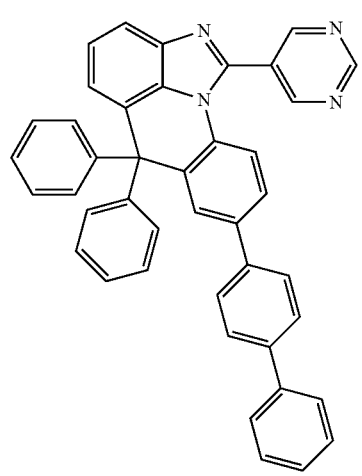
[B-40]
-continued
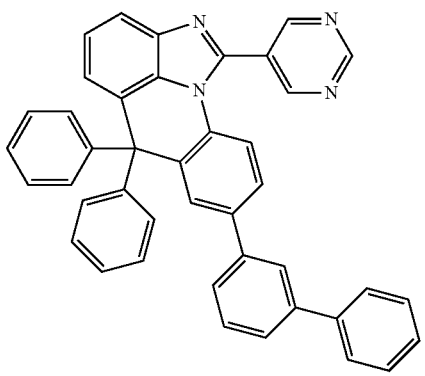
[B-41]
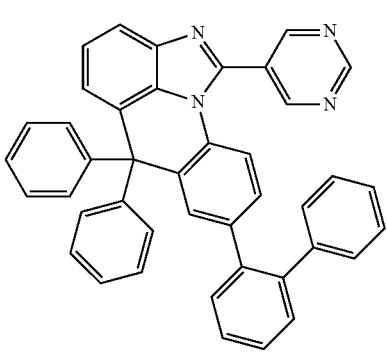
[B-42]
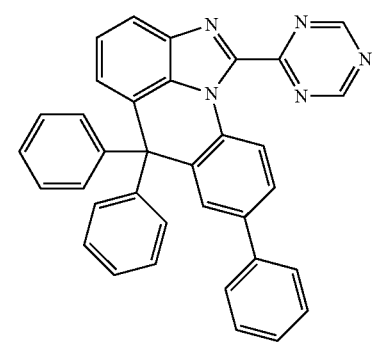
[B-43]
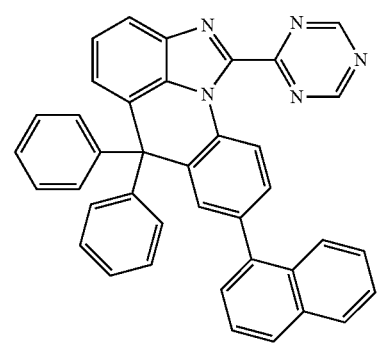
[B-44]

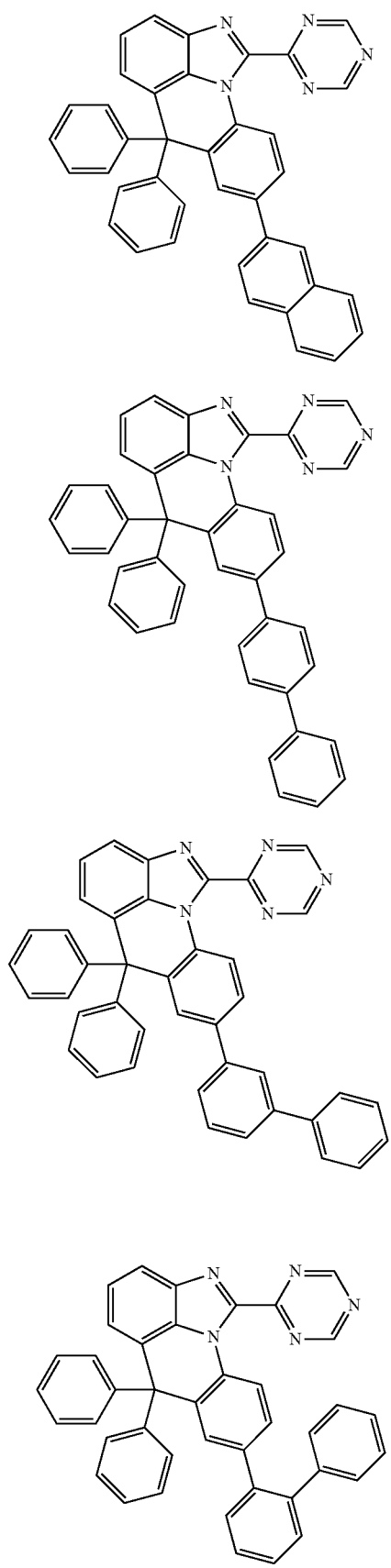
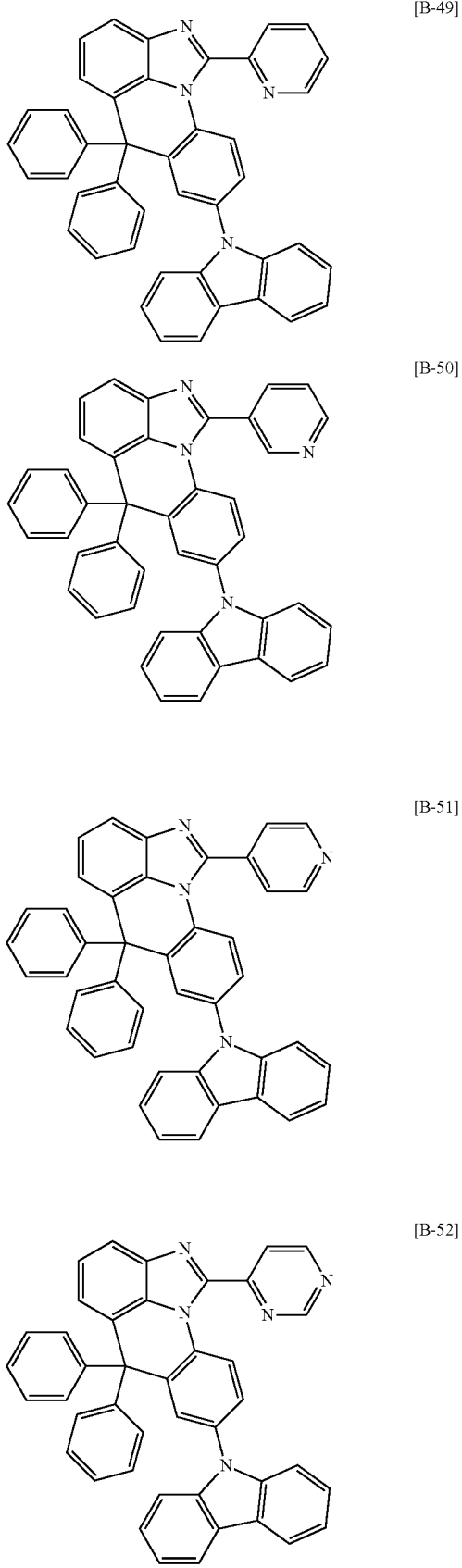

[B-53]
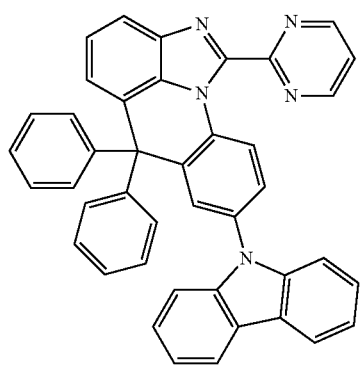
[B-57]
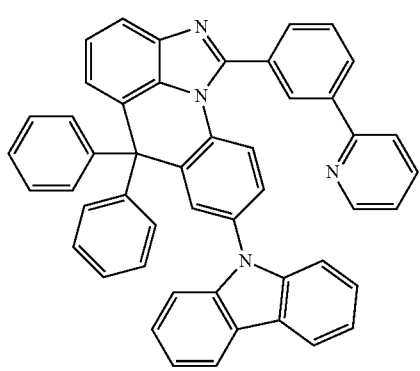
[B-54]
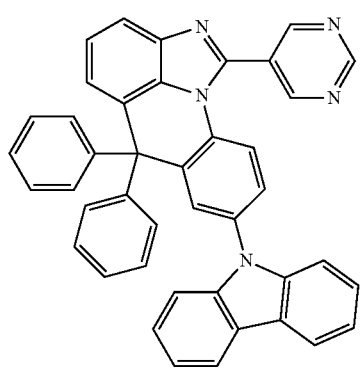
[B-55]
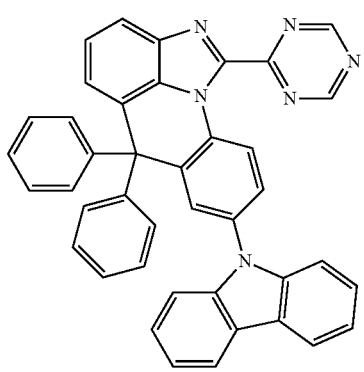
[B-58]
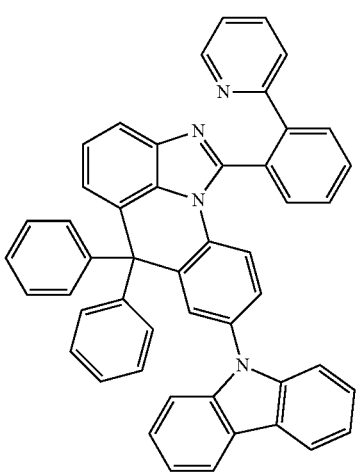
[B-56]
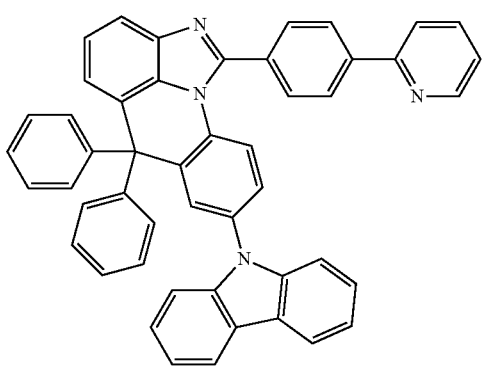
[B-59]
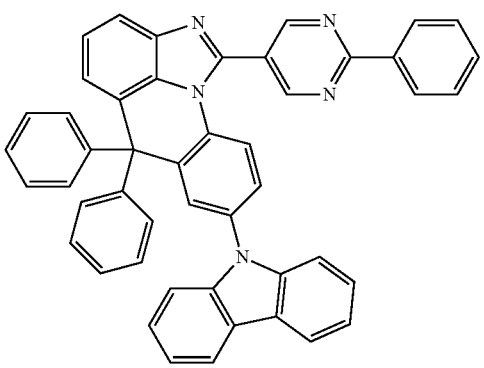

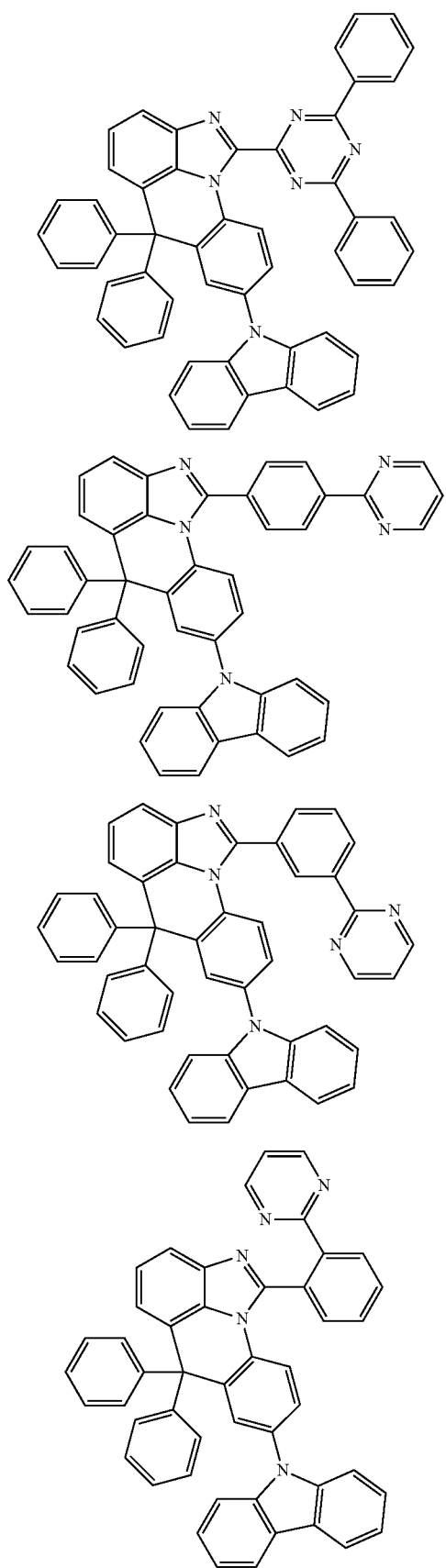
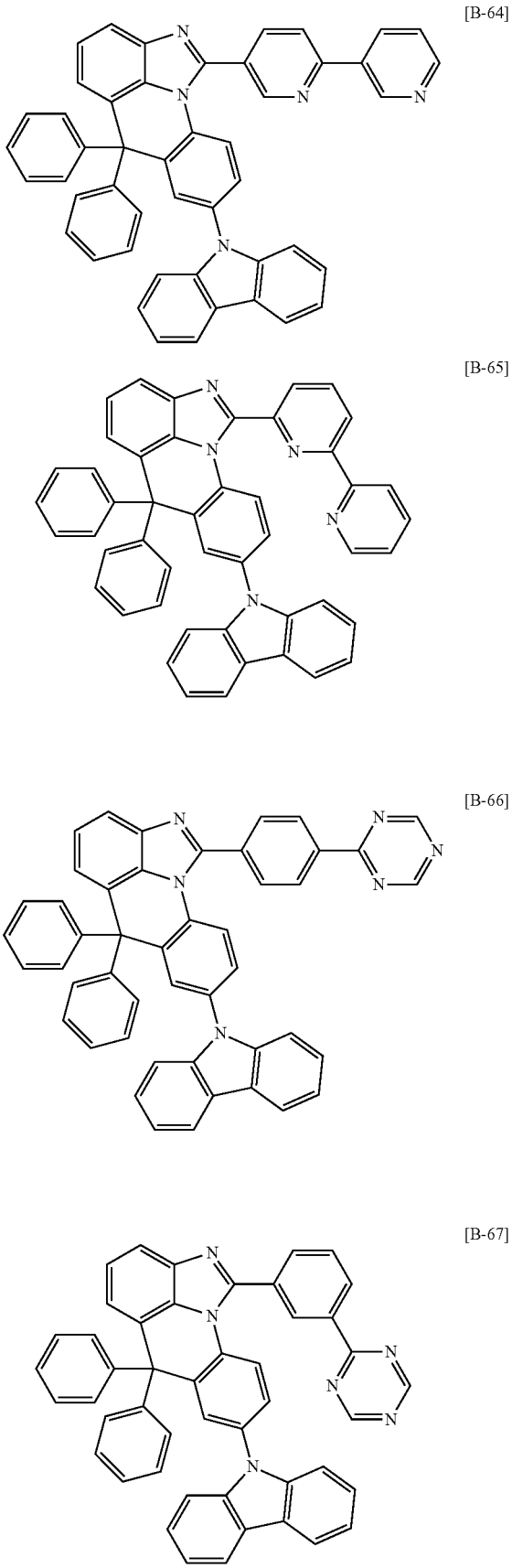

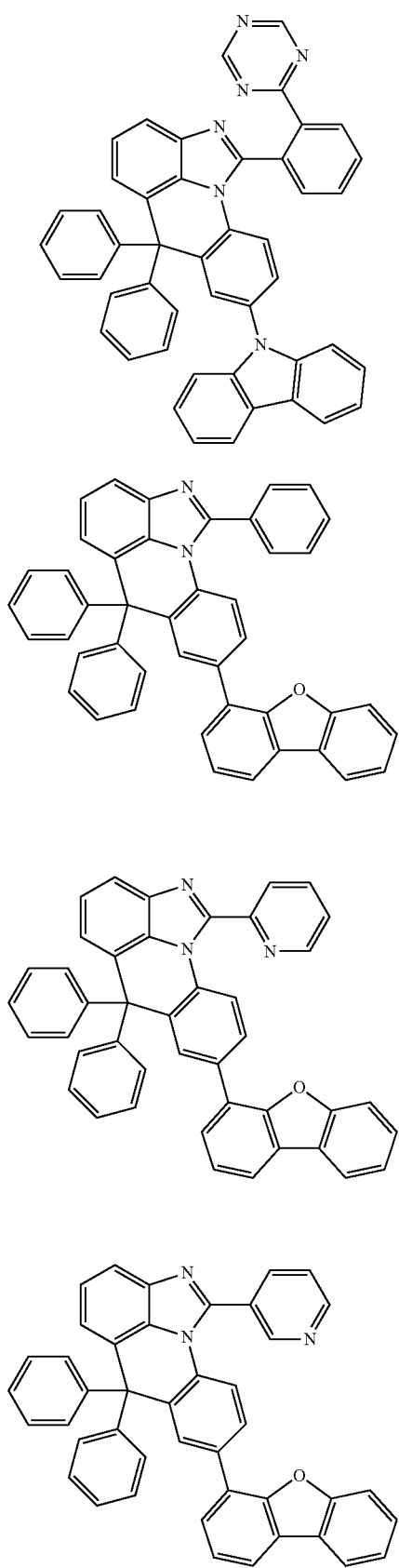

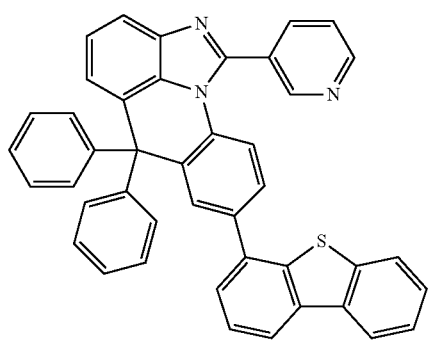
[B-76]
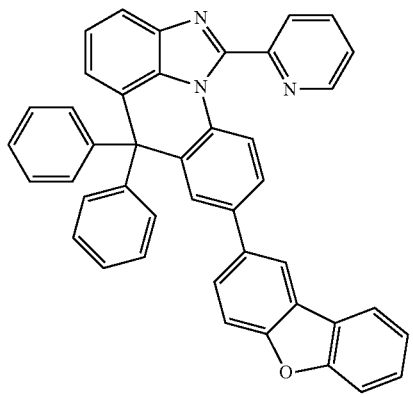
[B-80]
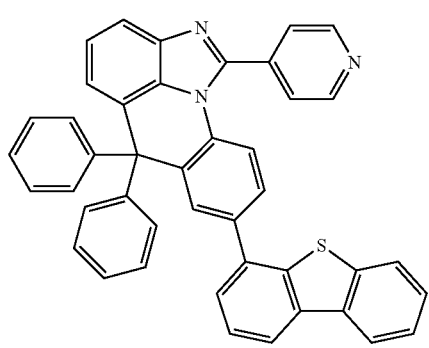
[B-77]
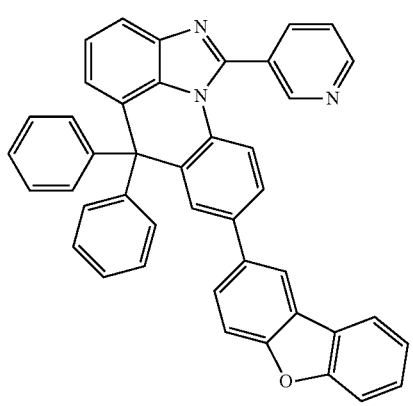
[B-81]
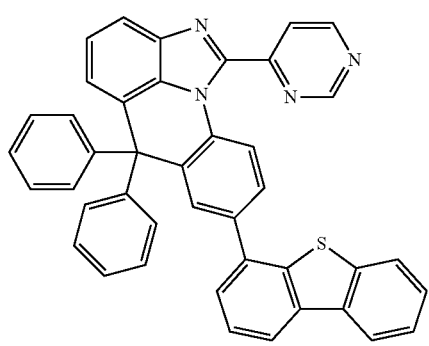
[B-78]
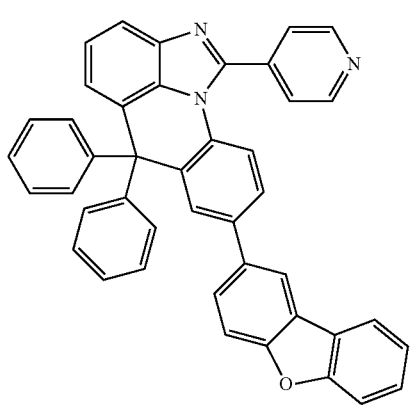
[B-82]
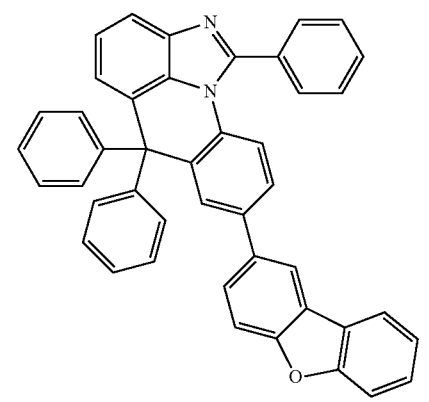
[B-79]
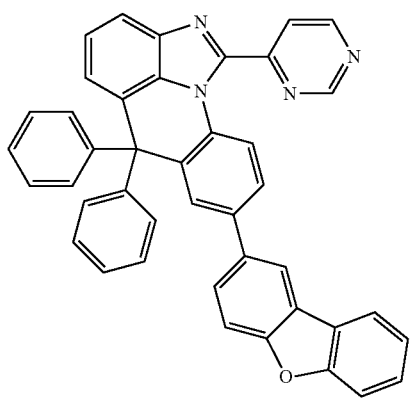
[B-83]

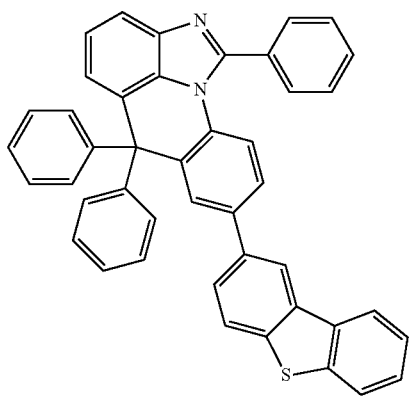
[B-84]
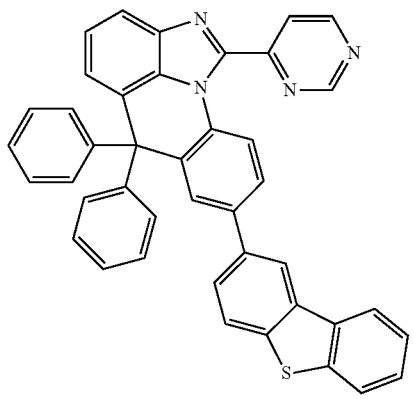
[B-88]
[B-85]
[B-89]
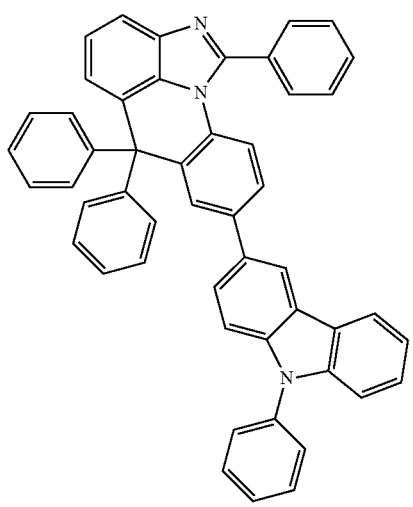
[B-86]
[B-87]
[B-90]
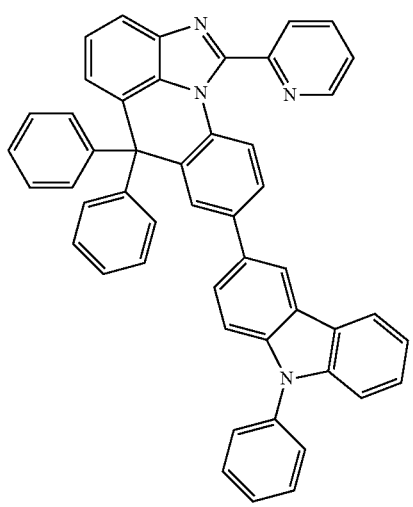

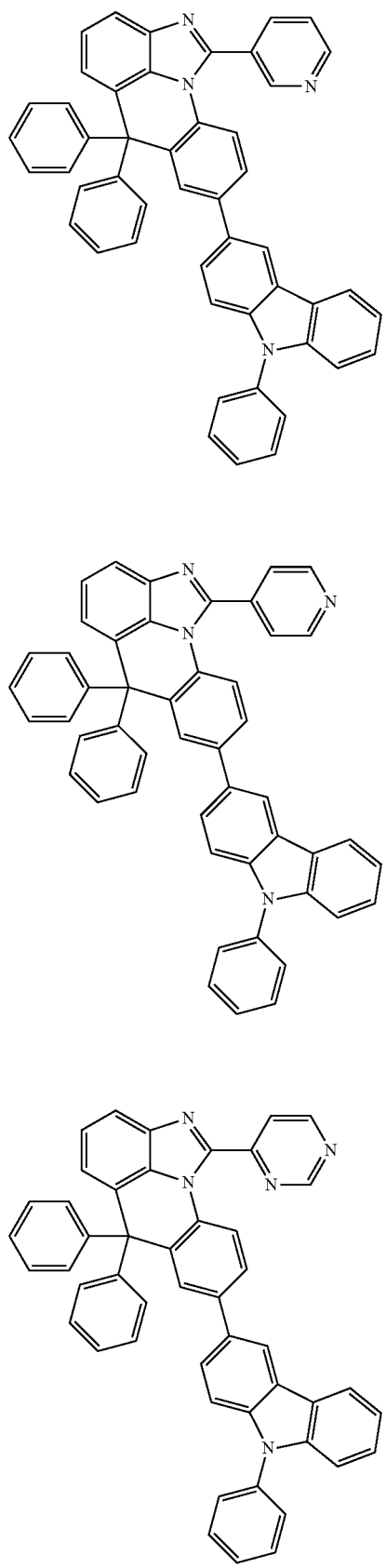
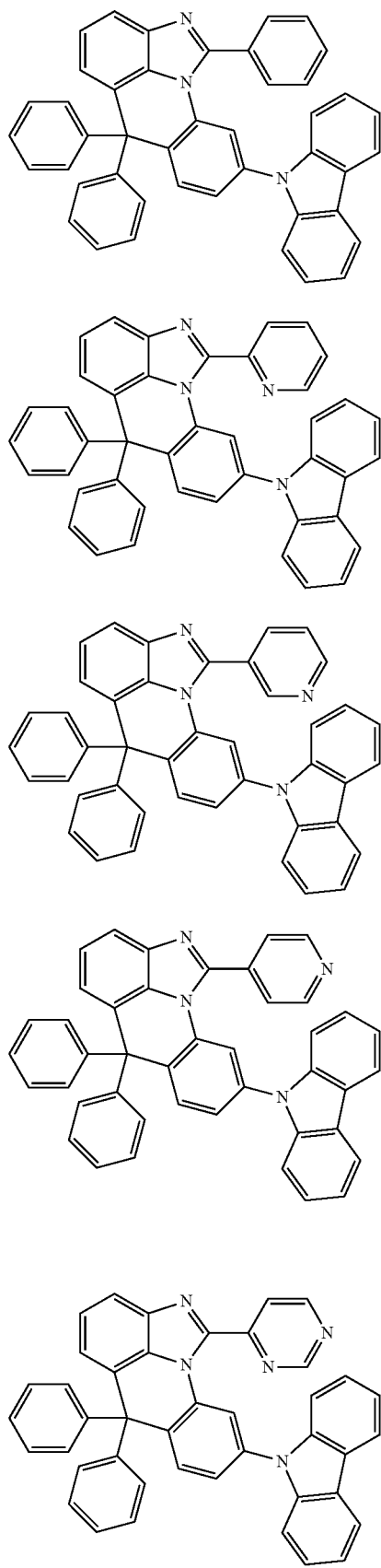

-continued
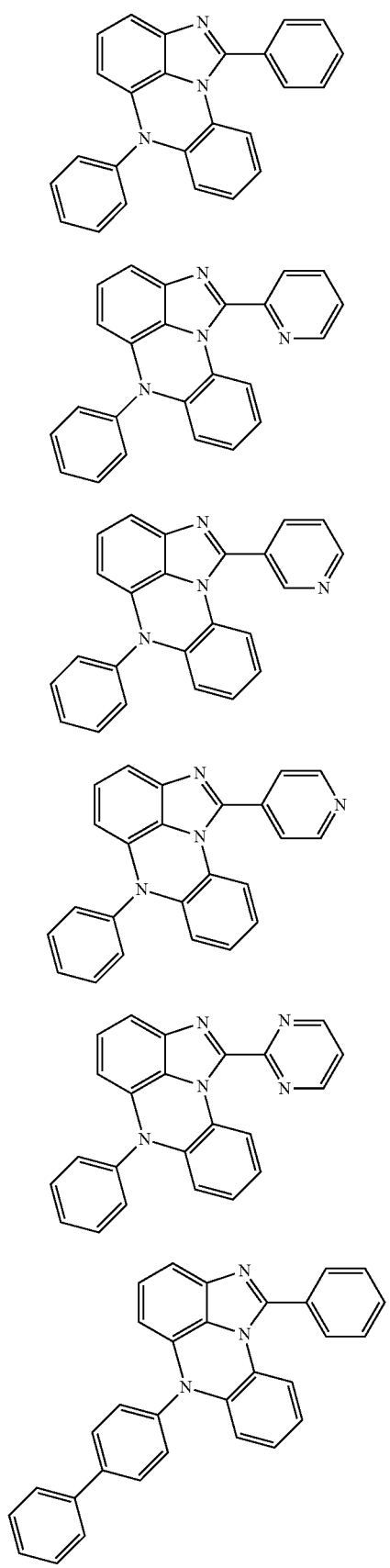
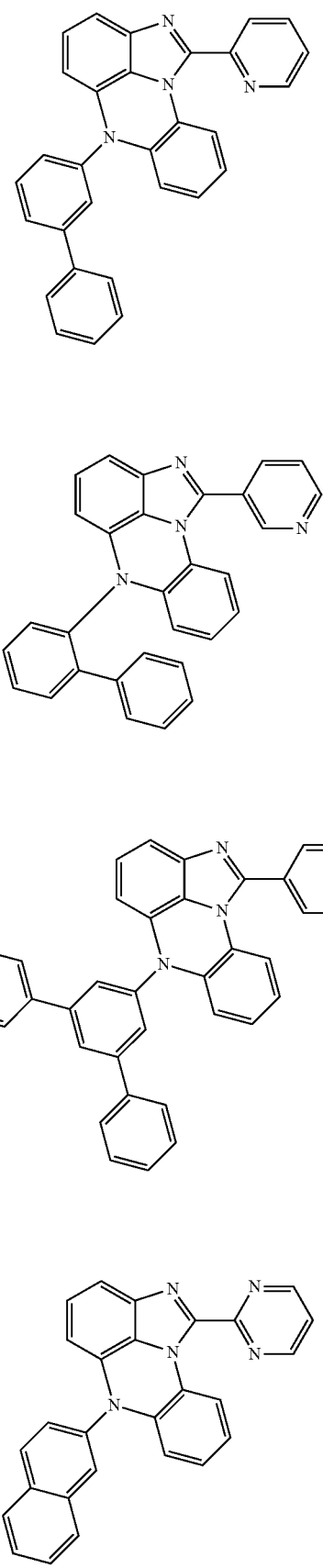

[C-11]
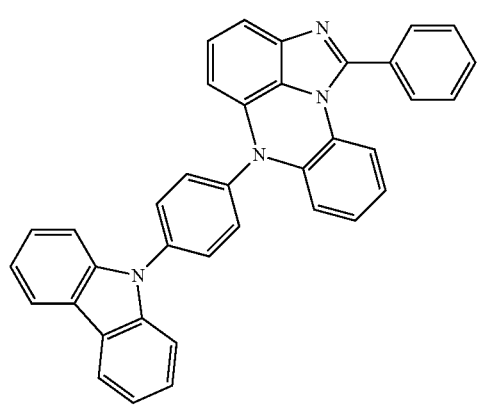
[C-12]
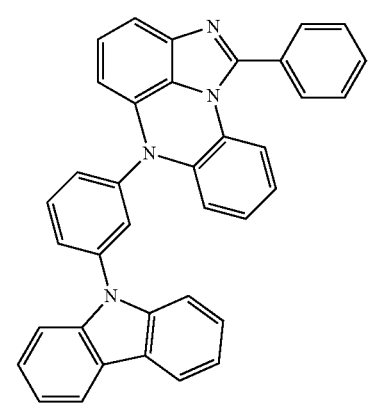
[C-13]
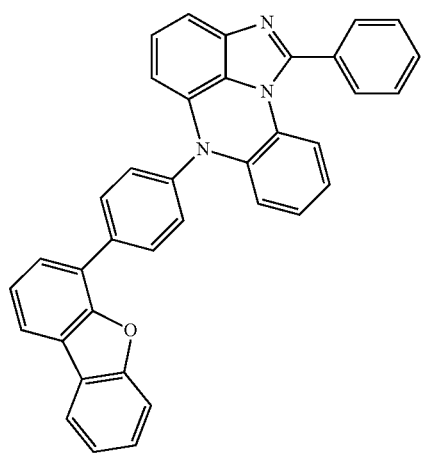
[C-14]
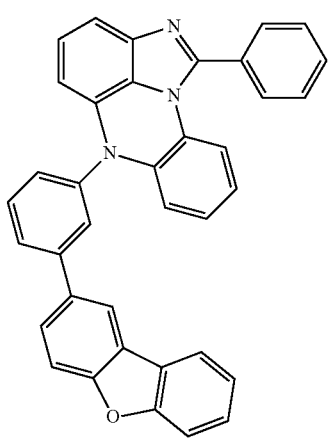
[C-15]
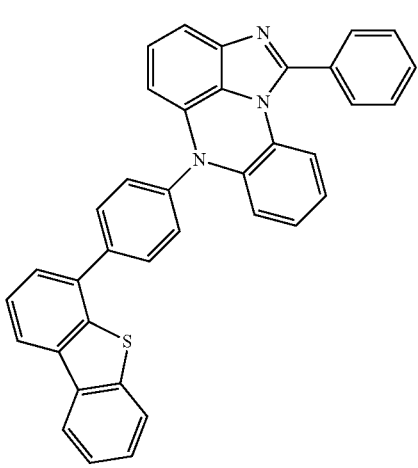
[C-16]
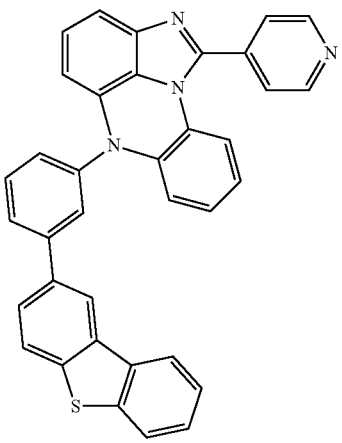

[C-17]
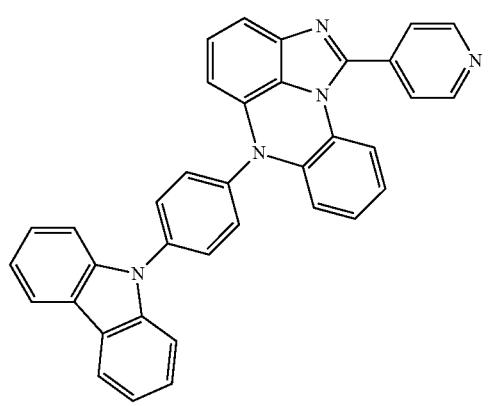

[C-18]
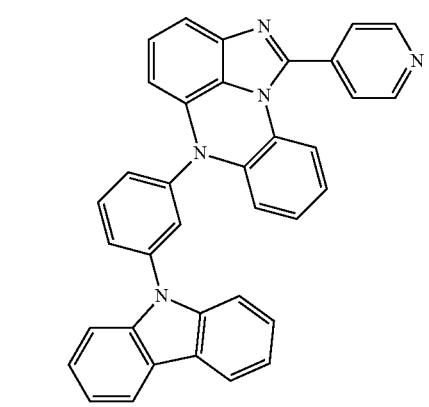

[C-19]
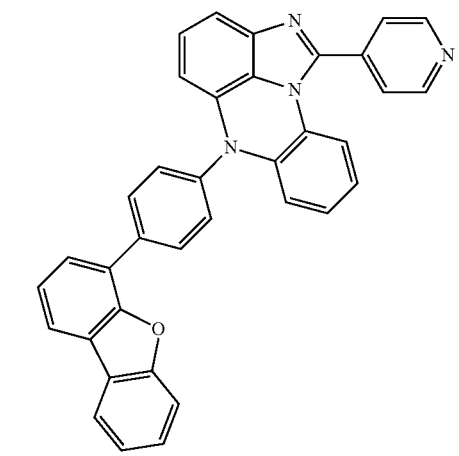

[C-20]
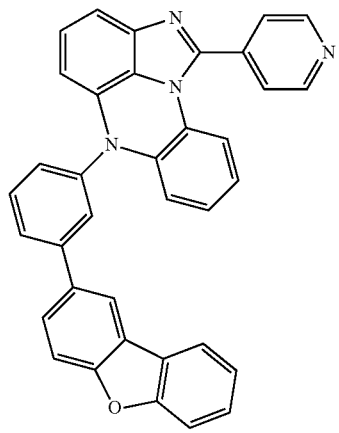

[C-21]
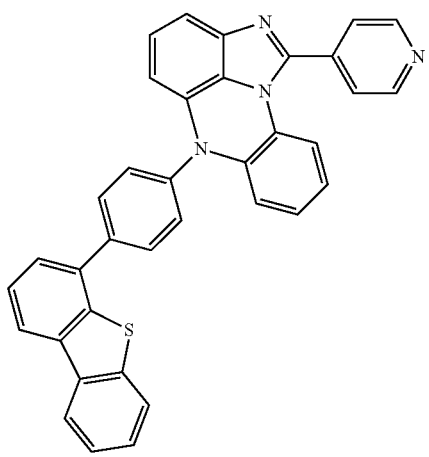

[C-22]
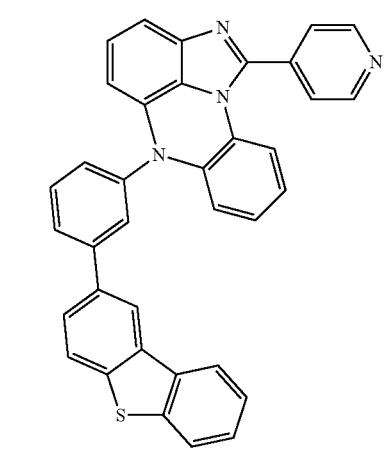

The compound of the present invention may be a compound having a triplet exciton energy (T1) of 2.0 eV or greater.

Hereinafter, an organic optoelectronic device including the compound is described.

The organic optoelectronic device may be any device to convert electrical energy into photoenergy and vice versa without particular limitation, and may be, for example an organic photoelectric device, an organic light emitting diode, an organic solar cell, and an organic photo-conductor drum.

Herein, an organic light emitting diode as one example of an organic optoelectronic device is described.

FIGS. 1 and 2 are cross-sectional views of an organic light emitting diode according to one embodiment.

Referring to FIG. 1, an organic optoelectronic device 100 according to one embodiment includes an anode 120 and a cathode 110 facing each other and an organic layer 105 between the anode 120 and the cathode 110.

The anode 120 may be made of a conductor having a high work function to help hole injection, for example metal, a metal oxide and/or a conductive polymer. The anode 120 may include, for example a metal or an alloy thereof such as nickel, platinum, vanadium, chromium, copper, zinc, and gold; metal oxide such as zinc oxide, indium oxide, indium tin oxide (ITO), and indium zinc oxide (IZO); a combination of a metal and an oxide such as ZnO and Al or $SnO_2$ and Sb; a conductive polymer such as poly (3-methylthiophene), poly (3,4-(ethylene-1,2-dioxy)thiophene) (PEDT), polypyrrole and polyaniline, but is not limited thereto.

The cathode 110 may be made of a conductor having a low work function to help electron injection, for example a metal, a metal oxide and/or a conductive polymer. The cathode 110 may include, for example a metal or an alloy thereof such as magnesium, calcium, sodium, potassium, titanium, indium, yttrium, lithium, gadolinium, aluminum silver, tin, lead, cesium, barium, and the like; a multi-layer structured material such as LiF/Al, $LiO_2$/Al, LiF/Ca, LiF/Al and $BaF_2$/Ca, but is not limited thereto.

The organic layer 105 includes an emission layer 130 including the compound.

The emission layer 130 may include, for example the compound at alone or with at least two of the compounds, or as a mixture with other different compound from the compound. When the compound is mixed with the other compound, for example they may be included as a host and a dopant, wherein the compound may be, for example included as a host. The host may be, for example phosphorescent host or fluorescent host, for example a green phosphorescent host.

When the compound is included as a host, the dopant may be selected from well-known inorganic, organic, organic/inorganic compound as a dopant.

Referring to FIG. 2, an organic light emitting diode 200 further includes a hole auxiliary layer 140 as well as an emission layer 230. The hole auxiliary layer 140 may further increase hole injection and/or hole mobility between the anode 120 and emission layer 230 and block electrons. The hole auxiliary layer 140 may be, for example a hole transport layer, a hole injection layer, and/or an electron blocking layer, and may include at least one layer. The compound may be included in the emission layer 130 and/or the hole auxiliary layer 140.

Even though not shown in FIG. 1 or FIG. 2, the organic layer 105 may further include an electron injection layer (EIL), an electron transport layer (ETL), an auxiliary electron transport layer (ETL), a hole transport layer (HTL), an auxiliary hole transport layer (HTL), a hole injection layer (HIL), or a combination thereof. The compound of the present invention may be included in the organic layers. The organic light emitting diodes 100 and 200 may be manufactured by forming an anode or a cathode on a substrate, forming an organic layer in accordance with a dry coating method such as evaporation, sputtering, plasma plating, and ion plating; or a wet coating method such as spin coating, dipping, and flow coating; and forming a cathode or an anode thereon.

The organic light emitting diode may be applied to an organic light emitting diode (OLED) display.

Hereinafter, the embodiments are illustrated in more detail with reference to examples. These examples, however, are not in any sense to be interpreted as limiting the scope of the invention.

(Preparation of Compound for Organic Optoelectronic Device)

Compound for Organic Photoelectric Device

[General Formula 1]

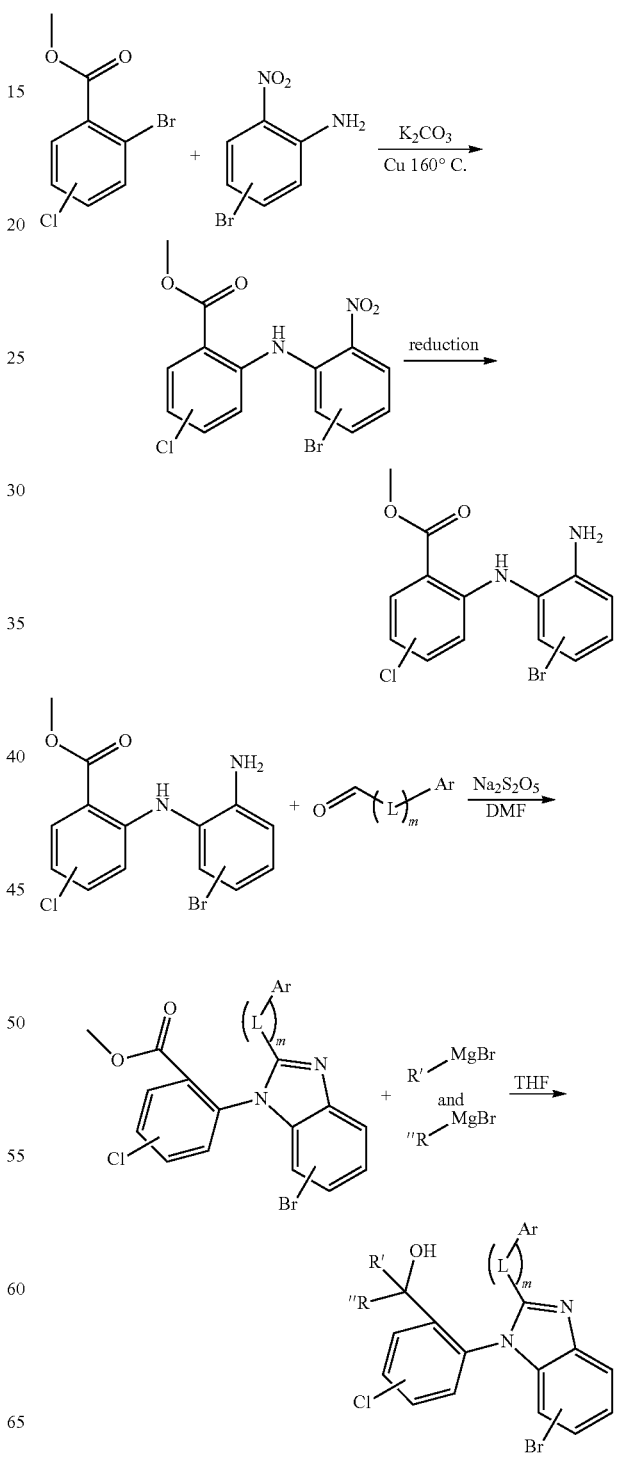

-continued
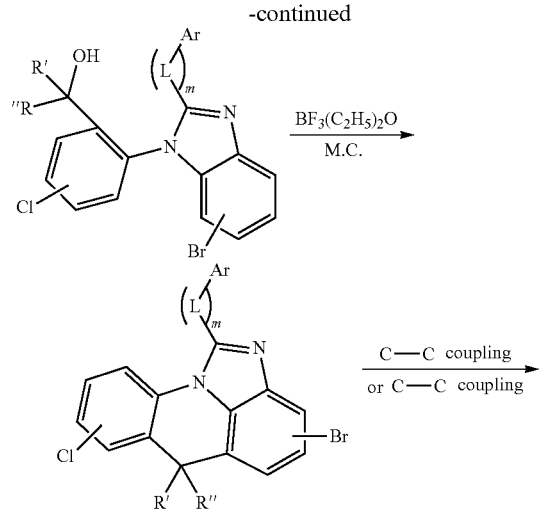
-continued
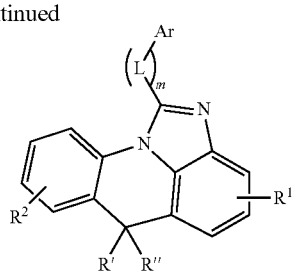
Specific compounds manufactured in the above synthesis method according to one embodiment of the present invention are provided in Table 1.
TABLE 1
| Compound | Intermediate D | Intermediate E |
|---|---|---|
| A-51 | | |
| A-77 | | |

TABLE 1-continued
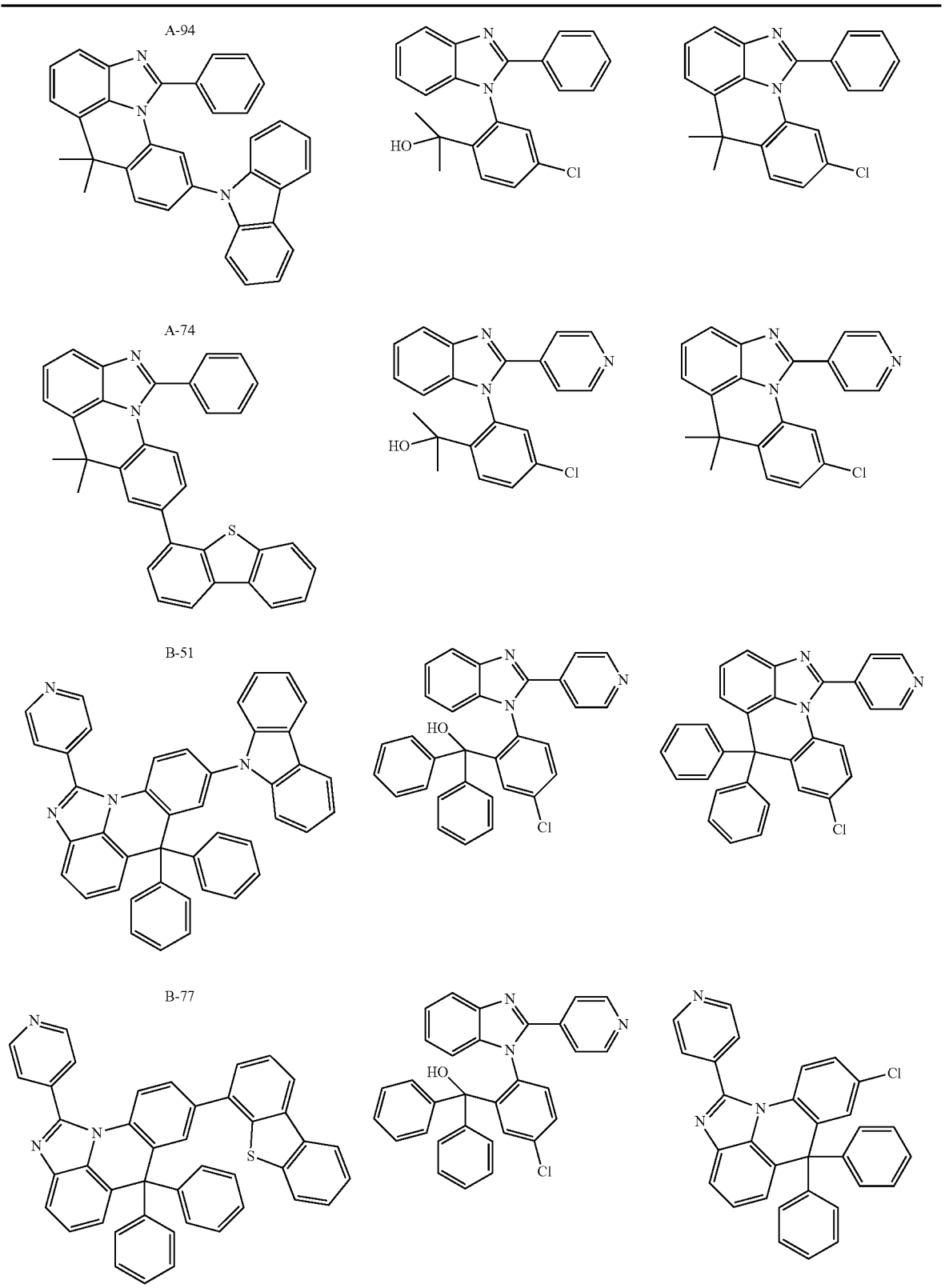

TABLE 1-continued
B-94
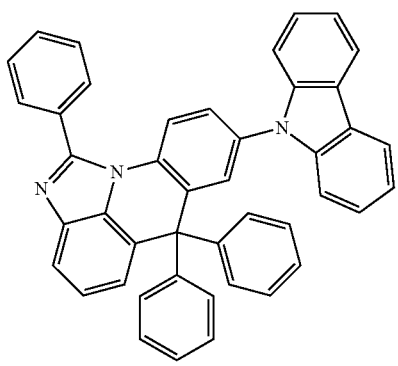
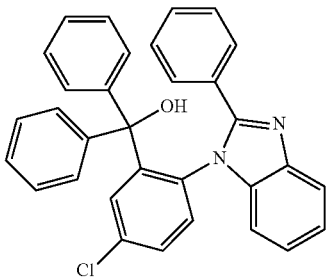 [SMILES: OC(c1ccccc1)(c1ccccc1)c1cc(Cl)ccc1-n1c(-c2ccccc2)nc2ccccc21]
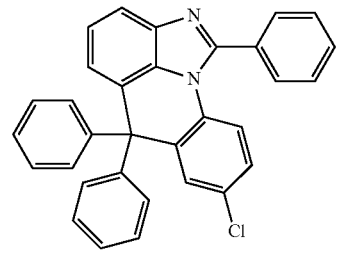 [SMILES: Clc1ccc2c(c1)C(c1ccccc1)(c1ccccc1)c1cccc3nc(-c4ccccc4)n-2c13]
B-97
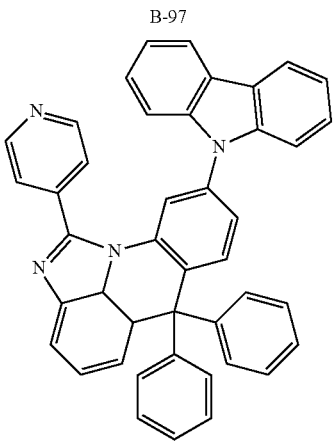
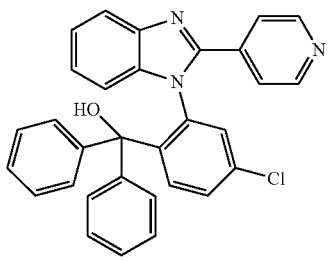 [SMILES: OC(c1ccccc1)(c1ccccc1)c1ccc(Cl)cc1-n1c(-c2ccncc2)nc2ccccc21]
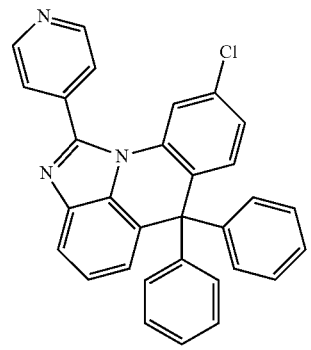 [SMILES: Clc1ccc2c(c1)-n1c(-c3ccncc3)nc3cccc(c31)C2(c1ccccc1)c1ccccc1]
C-11
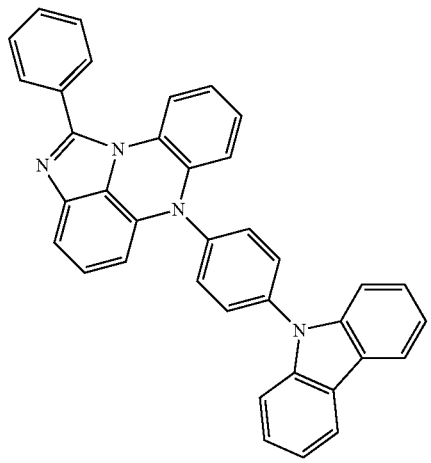
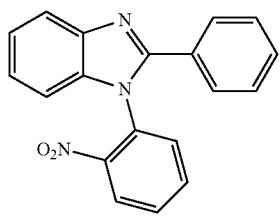 [SMILES: O=[N+]([O-])c1ccccc1-n1c(-c2ccccc2)nc2ccccc21]
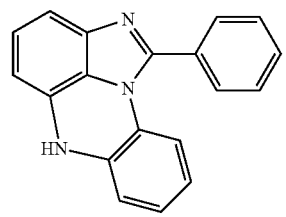 [SMILES: c1ccc(-c2nc3cccc4c3n2-c2ccccc2N4)cc1]

TABLE 1-continued
C-15
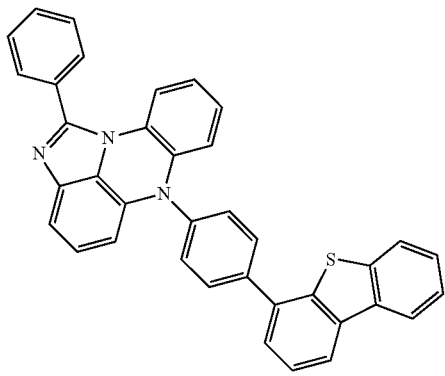
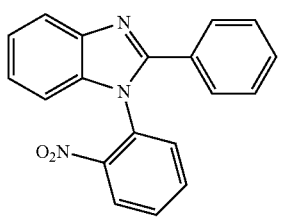 [SMILES: O=[N+]([O-])c1ccccc1-n1c(-c2ccccc2)nc2ccccc21]
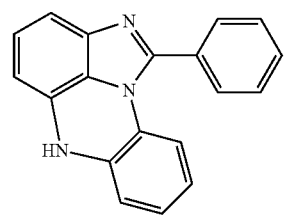 [SMILES: c1ccc(-c2nc3cccc4c3n2-c2ccccc2N4)cc1]
C-17
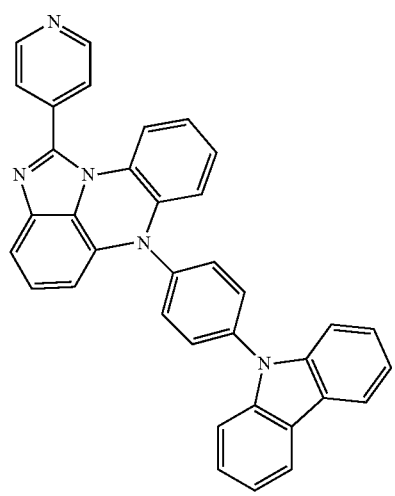
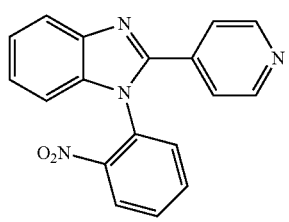 [SMILES: O=[N+]([O-])c1ccccc1-n1c(-c2ccncc2)nc2ccccc21]
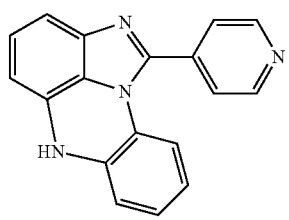 [SMILES: c1ccc2c(c1)Nc1cccc3nc(-c4ccncc4)n-2c13]
C-21
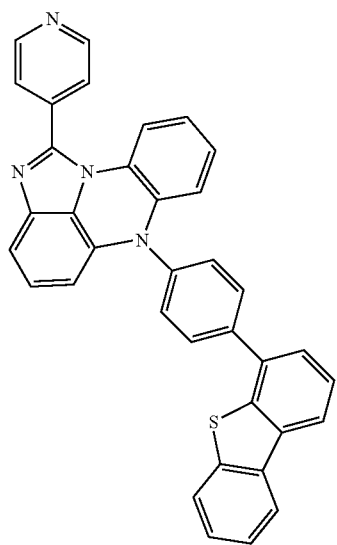
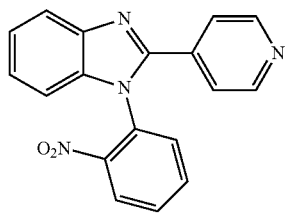 [SMILES: O=[N+]([O-])c1ccccc1-n1c(-c2ccncc2)nc2ccccc21]
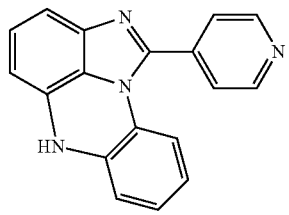 [SMILES: c1ccc2c(c1)Nc1cccc3nc(-c4ccncc4)n-2c13]

TABLE 1-continued
| Compound | Reactant | Yield (%) | MS data |
|---|---|---|---|
| A-51 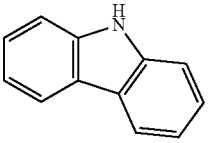 [SMILES: c1ccc2c(c1)[nH]c1ccccc12] | 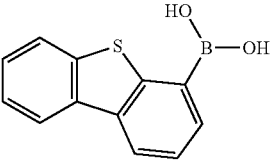 [SMILES: OB(O)c1cccc2c1sc1ccccc12] | 83 | 476.6 g/mol |
| A-77 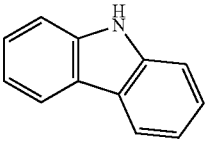 [SMILES: c1ccc2c(c1)[nH]c1ccccc12] | 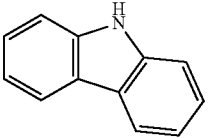 [SMILES: c1ccc2c(c1)[nH]c1ccccc12] | 80 | 493.6 g/mol |
| A-94 | | 80 | 475.6 g/mol |
| A-74 | | 85 | 476.6 g/mol |

TABLE 1-continued

| | | | |
|---|---|---|---|
| B-51 | | 84 | 600.7 g/mol |
| B-77 | | 80 | 617.8 g/mol |
| B-94 | | 87 | 599.7 g/mol |
| B-97 | | 89 | 600.7 g/mol |

TABLE 1-continued

| | | | |
|---|---|---|---|
| C-11 (structure) | (structure with Br) | 88 | 524.6 g/mol |
| C-15 (structure) | (structure with Br) | 85 | 541.7 g/mol |
| C-17 (structure) | (structure with Br) | 87 | 525.6 g/mol |

| | C-21 | | Br | 81 | 542.7 g/mol |
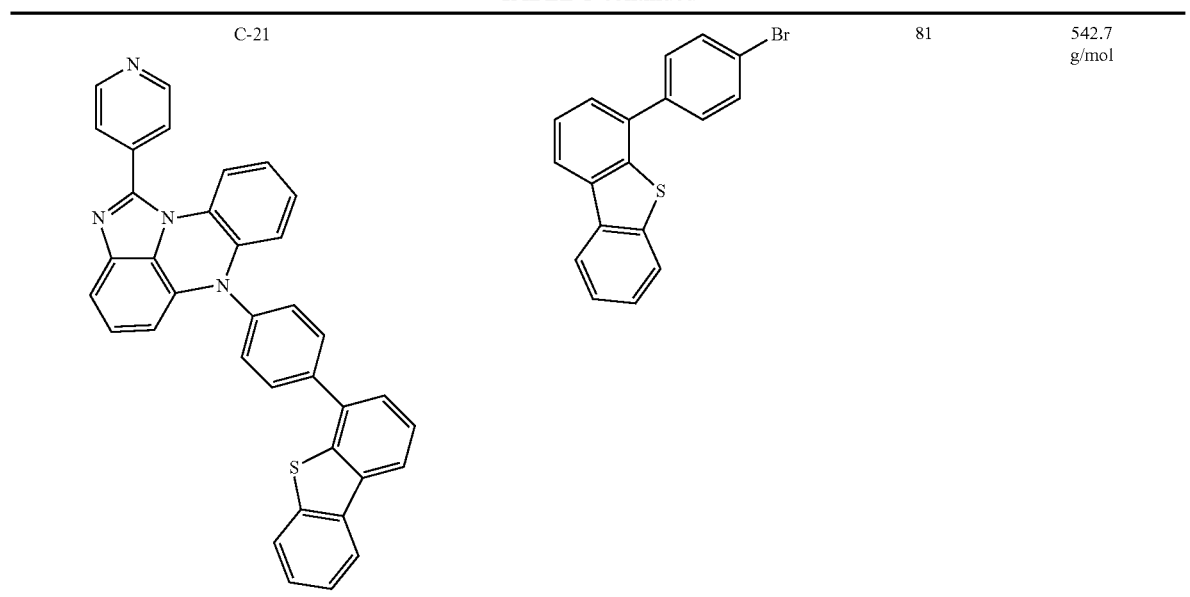
EXAMPLE 1: SYNTHESIS OF COMPOUND B-94
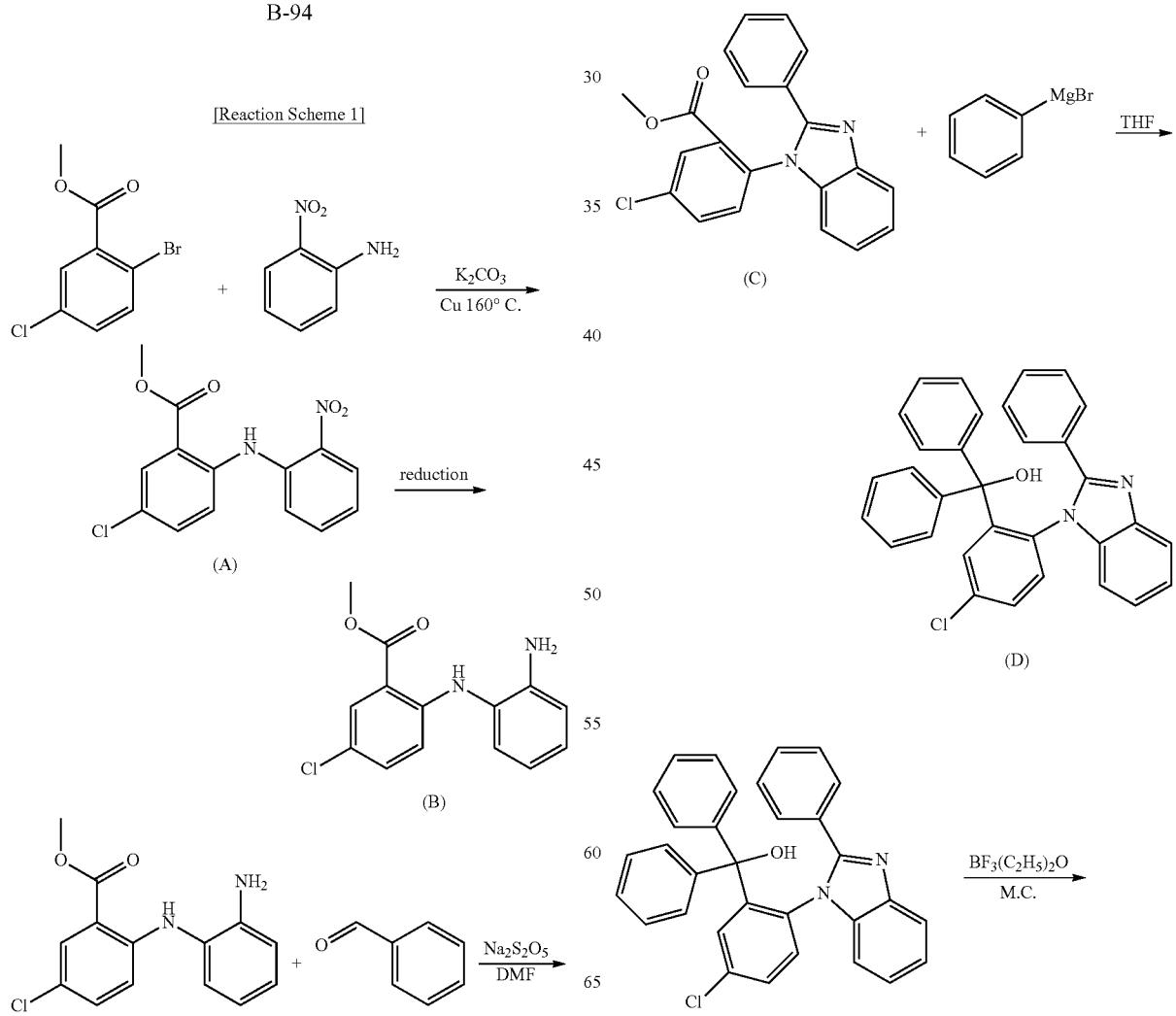

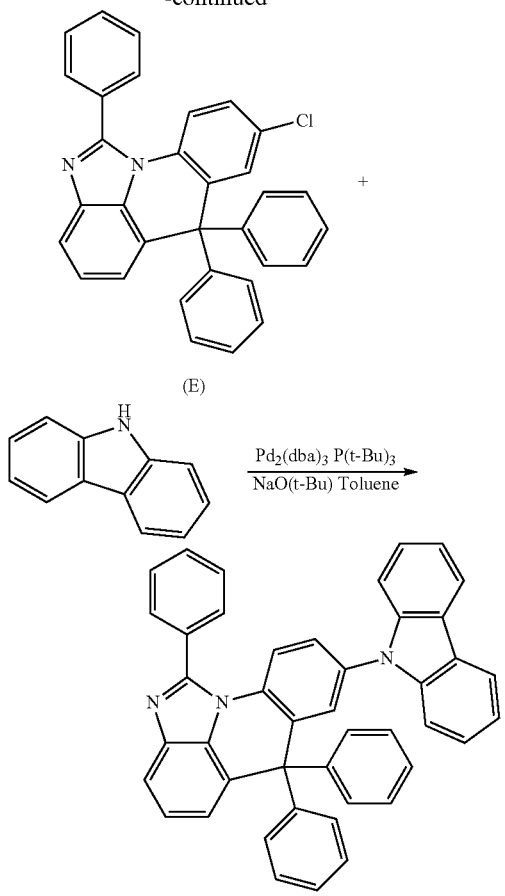

First Step: Synthesis of Intermediate Product A 36.12 g (144.79 mmol) of 2-bromo-5-chloro-benzoic acid methyl ester, 20.0 g (144.79 mmol) of 2-nitro-phenylamine, 0.28 g (4.34 mmol) of Cu, and 30.02 g (217.19 mmol) of $K_2CO_3$ were agitated at 160° C. under a nitrogen stream for 36 hours. When the reaction was complete, a product therein was dissolved in dichloromethane and silica filtered, and an organic solvent was removed therefrom. The residue was silica gel columned with hexane:dichloromethane=7:3 (v/v), obtaining 24.88 g of an intermediate product A (a yield: 56%).

Second Step: Synthesis of Intermediate Product B 24.0 g (78.25 mmol) of the intermediate product A and 44.51 g (234.76 mmol) of $SnCl_2.2H_2O$ were suspended in 200 ml of ethanol, and the suspended resultant was agitated under a nitrogen stream for 12 hours at 80° C. When the reaction was complete, a product therein was dissolved in dichloromethane and silica-filtered with dichloromethane and ethylacetate, and an organic solvent was removed therefrom. The residue was silica columned with hexane:ethylacetate=6:4 (v/v), obtaining 14.4 g of an intermediate product B (a yield: 70%).

Third Step: Synthesis of Intermediate Product C 14.0 g (53.29 mmol) of the intermediate product B and 5.65 g (53.29 mmol) of benzoaldehyde were suspended in 170 mL of DMF, 12.16 g (63.95 mmol) of $Na_2S_2O_5$ was added thereto, and the mixture was agitated under a nitrogen stream for 5 hours at 150° C. The resultant was extracted with dichloromethane and distilled water, and an organic layer was silica gel filtered. Then, an organic solution was removed therefrom, and the residue was silica gel columned with hexane:dichloromethane=7:3 (v/v), obtaining 18.37 g of an intermediate product C (a yield: 95%).

Fourth Step: Synthesis of Intermediate Product D 18.0 g (49.61 mmol) of the intermediate product C and 150 mL of THF were suspended under a nitrogen stream, 124.03 mL (124.03 mmol) of BrMgPh was slowly added thereto at 0° C., and the mixture was agitated for 24 hours. When the reaction was complete, the resultant was quenched at 0° C. with ammonium chloride and extracted with dichloromethane and distilled water, and an organic solvent was removed therefrom, obtaining 22.5 g of an intermediate product (D) (a yield: 93%).

Fifth Step: Synthesis of Intermediate Product E 22.5 g (46.20 mmol) of the intermediate product D and 150 mL of dichloromethane were suspended under a nitrogen stream at 0° C., 8.55 mL (69.30 mmol) of $BF_3(C_2H_5)2O$ was slowly added thereto, and the mixture was agitated for 12 hours. When the reaction was complete, the resultant was quenched with $NaHCO_3$ at 0° C. and extracted with dichloromethane and distilled water, an organic solvent was removed therefrom, and the residue was recrystallized with dichloromethane and ethylacetate, obtaining 16.5 g of an intermediate product E (a yield: 76%).

Sixth Step: Synthesis of Compound B-94

16.0 g (34.12 mmol) of the intermediate product E, 6.85 g (40.94 mmol) of carbazole, 4.92 g (51.17 mmol) of NaO(t-Bu), and 0.62 g (0.68 mmmol) of $Pd_2(dba)_3$ were suspended in 150 mL of toluene, 0.33 mL (1.36 mmol) of $P(t-Bu)_3$ was added thereto, and the mixture was refluxed and agitated under a nitrogen stream for 24 hours. The resultant was extracted with dichloromethane and distilled water, and an organic layer was silica gel filtered therefrom. Then, an organic solution was removed, and the residue was silica gel columned with hexane:dichloromethane=7:3 (v/v) and recrystallized with dichloromethane and ethylacetate, obtaining 17.8 g of a compound B-94 (a yield: 87%).

EXAMPLE 2: SYNTHESIS OF COMPOUND B-51

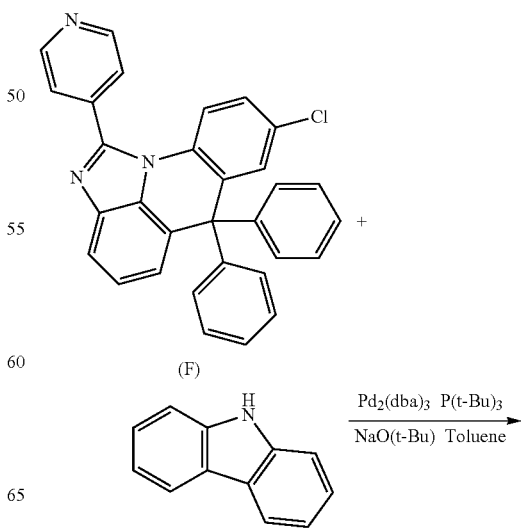

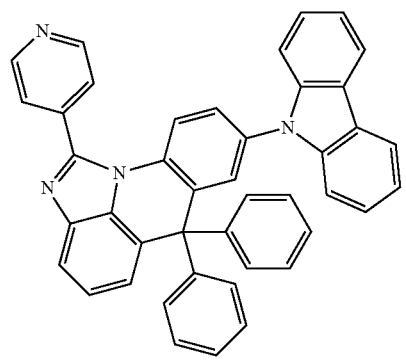

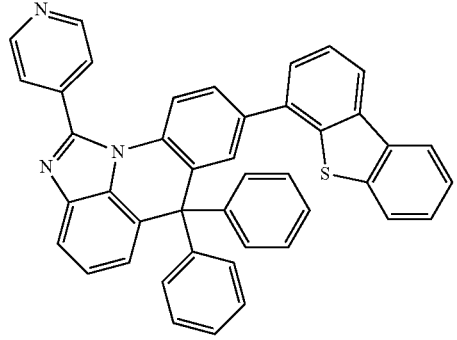

10.0 g (21.28 mmol) of the intermediate product F obtained according to the same method as Example 1 except for using pyridine-4-carboaldehyde instead of the benzoaldehyde in the third step of Example 1, 6.85 g (27.66 mmol) of carbazole, 3.07 g (31.92 mmol) of NaO(t-Bu), and 0.39 g (0.43 mmmol) of $Pd_2(dba)3$ were suspended in 100 mL of toluene, 0.21 mL (0.85 mmol) of $P(t-Bu)_3$ was added thereto, and the mixture was refluxed and agitated under a nitrogen stream for 24 hours. The resultant was extracted with dichloromethane and distilled water, and an organic layer was silica gel filtered therefrom. Then, a organic solution was removed therefrom, and the residue was silica gel columned with hexane:dichloromethane=7:3 (v/v) and recrystallized with dichloromethane and ethylacetate, obtaining 10.7 g of a compound B-51 (a yield: 84%).

10.0 g (21.28 mmol) of the intermediate product F, 5.34 g (23.41 mmol) of 4-dibenzothiophene boronic acid, 5.88 g (42.56 mmol) of $K_2CO_3$, and 0.25 g (0.21 mmol) of $Pd(PPh_3)_4$ were suspended in 100 ml of toluene and 50 ml of distilled water, and the suspended resultant was refluxed and agitated under a nitrogen stream for 12 hours. When the reaction was complete, the reaction solution was extracted with dichloromethane, silica gel-filtered, distillated under a reduced pressure, silica-columned with hexane:dichloromethane=8:2 (v/v), and recrystallized with dichloromethane and ethylacetate, obtaining 10.5 g of a compound B-77 (a yield: 80%).

EXAMPLE 3: SYNTHESIS OF COMPOUND B-77

EXAMPLE 4: SYNTHESIS OF COMPOUND B-97

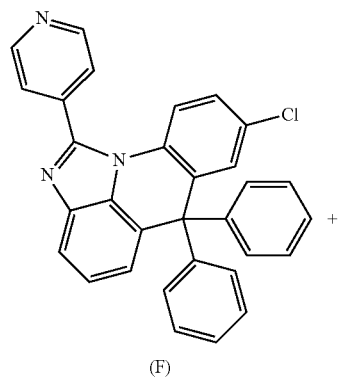

(F)

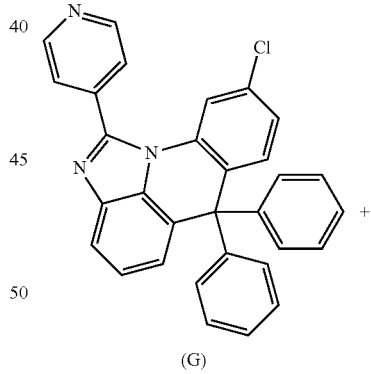

(G)

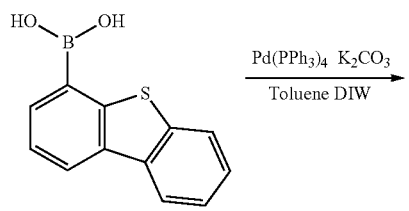

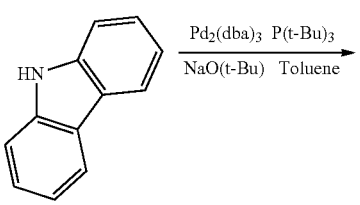

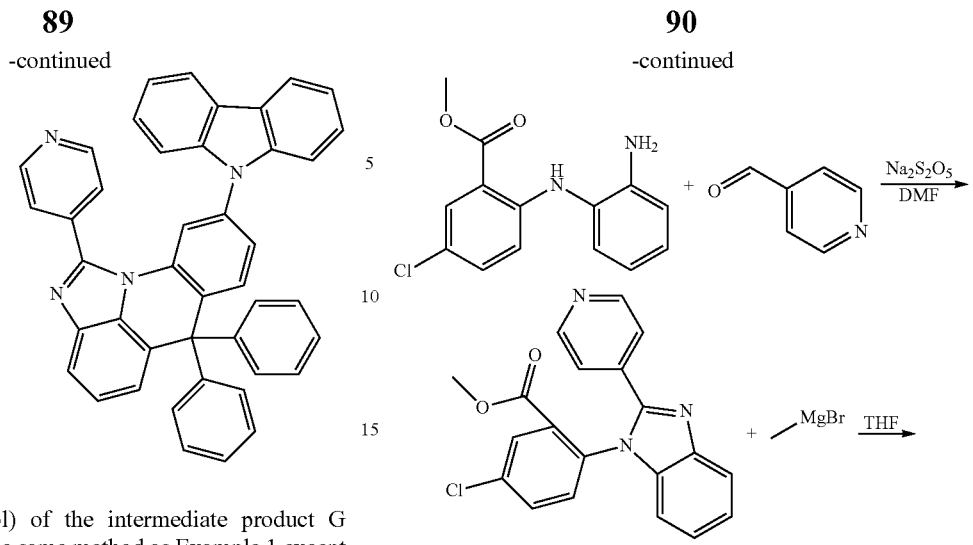

10.0 g (21.28 mmol) of the intermediate product G obtained according to the same method as Example 1 except for using 2-bromo-4-chloro-benzoic acid methyl ester instead of the 2-bromo-5-chloro-benzoic acid methyl ester in the first step of Example 1, 6.85 g (27.66 mmol) of carbazole, 3.07 g (31.92 mmol) of NaO(t-Bu), and 0.39 g (0.43 mmmol) of Pd$_2$(dba)$_3$ were suspended in 100 mL of toluene, 0.21 mL (0.85 mmol) of P(t-Bu)$_3$ was added thereto, and the mixture was refluxed and agitated under a nitrogen stream for 24 hours. The resultant was extracted with dichloromethane and distilled water, and an organic layer therein was silica gel filtered. Then, an organic solution was removed, the residue was silica gel column with hexane:dichloromethane=7:3 (v/v) and then, recrystallized with dichloromethane and ethylacetate, obtaining 11.4 g of a compound B-97 (a yield: 89%).

EXAMPLE 5: SYNTHESIS OF COMPOUND A-51

[Reaction Scheme 2]

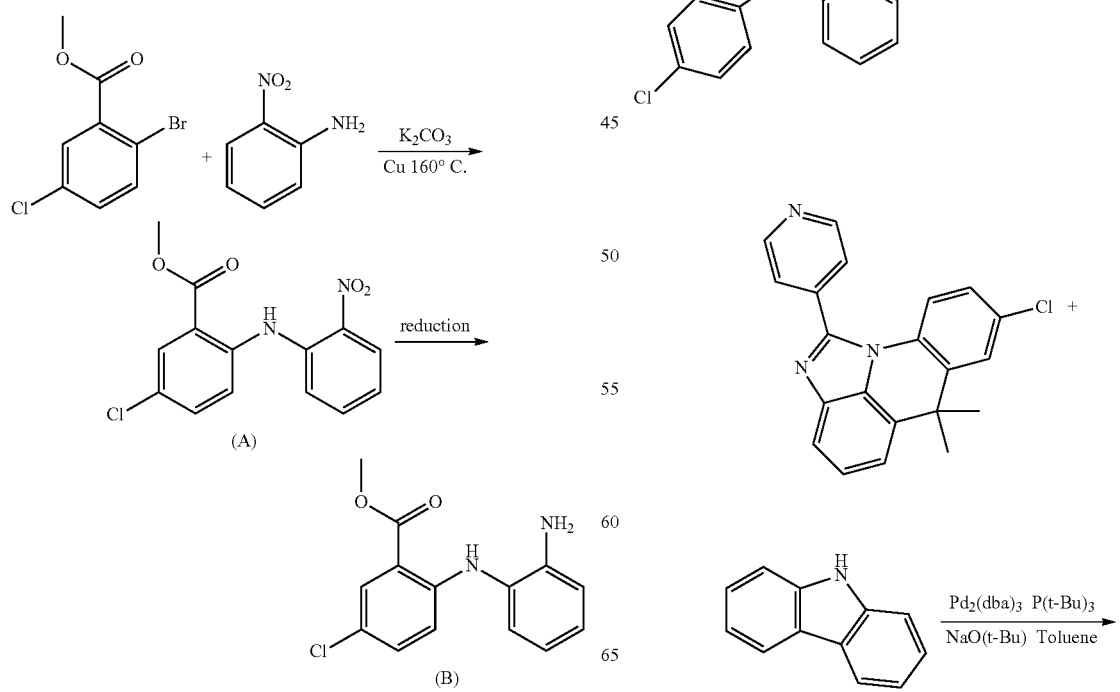

-continued

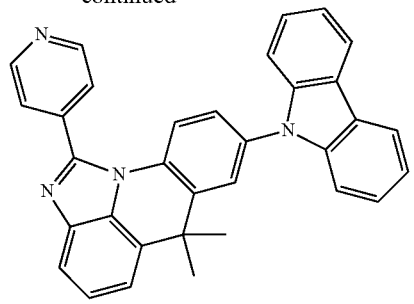

First Step; Synthesis of Intermediate Product (A)

36.12 g (144.79 mmol) of 2-bromo-5-chloro-benzoic acid methyl ester, 20.0 g (144.79 mmol) of 2-nitro-phenylamine, 0.28 g (4.34 mmol) of Cu, and 30.02 g (217.19 mmol) of $K_2CO_3$ were agitated under a nitrogen stream for 36 hours at 160° C. When the reaction was complete, a product therefrom was dissolved in dichloromethane and silica filtered, and an organic solvent was removed therefrom. The resultant was silica gel columned with hexane:dichloromethane=7:3 (v/v), obtaining 24.88 g of an intermediate product A (a yield: 56%).

Second Step; Synthesis of Intermediate Product B 24.0 g (78.25 mmol) of the intermediate product A and 44.51 g (234.76 mmol) of $SnCl_2.2H_2O$ were suspended in 200 ml of ethanol, and the suspended resultant was agitated under a nitrogen stream for 12 hours at 80° C. When the reaction was complete, a product therein was dissolved in dichloromethane and silica filtered with dichloromethane and ethylacetate, and an organic solvent was removed therefrom. The resultant was silica columned with hexane:ethylacetate=6:4 (v/v), obtaining 14.4 g of an intermediate product B (a yield: 70%).

Third Step: Synthesis of Intermediate Product C 15.0 g (54.21 mmol) of the intermediate product B and 6.06 mL (59.63 mmol) of 4-pyridinecarboaldehyde were suspended in 170 mL of DMF, 14.43 g (75.89 mmol) of $Na_2S_2O_5$ was added thereto, and the mixture was agitated under a nitrogen stream for 5 hours at 150° C. The resultant was extracted with dichloromethane and distilled water, an organic layer was silica gel filtered therefrom. Then, an organic solution was removed therefrom, and the residue was silica gel columned with hexane:ethylacetate=8:2 (v/v), obtaining 17.75 g of an intermediate product C (a yield: 90%).

Fourth Step: Synthesis of Intermediate Product D 15.0 g (41.23 mmol) of the intermediate product C was suspended in 150 mL of THF under a nitrogen stream, 32.96 mL (98.96 mmol) of BrMgMe was slowly added thereto at 0° C., and the mixture was agitated for 24 hours. When the reaction was complete, the resultant was quenched with ammonium chloride at 0° C. and extracted with dichloromethane and distilled water, and an organic solvent was removed therefrom, obtaining 13.7 g of an intermediate product (D a yield: 91%).

Fifth Step: Synthesis of Intermediate Product E 15.0 g (41.23 mmol) of the intermediate product D was suspended in 150 mL of dichloromethane under a nitrogen stream, 7.63 mL (61.84 mmol) of $BF_3(C_2H_5)2O$ was slowly added thereto, and the mixture was agitated for 12 hours. When the reaction was complete, the resultant was quenched with $NaHCO_3$ at 0° C. and extracted with dichloromethane and distilled water, an organic solvent was removed therefrom, and the residue was recrystallized with dichloromethane and ethylacetate, obtaining 9.3 g of an intermediate product E (a yield: 65%).

Sixth step: Synthesis of Compound A-51

10.0 g (28.92 mmol) of the intermediate product E, 5.80 g (34.70 mmol) of carbazole, 4.17 g (43.38 mmol) of NaO(t-Bu), and 0.53 g (0.59 mmmol) of Pd2(dba)3 were suspended in 150 mL of toluene, 0.28 mL (1.16 mmol) of $P(t-Bu)_3$ was added thereto, and the mixture was refluxed and agitated under a nitrogen stream for 24 hours. The resultant was extracted with dichloromethane and distilled water, and an organic layer was silica gel filtered. After removing an organic solution therefrom, the residue was silica gel column with hexane:ethylacetate=7:3 (v/v) and recrystallized with dichloromethane and ethylacetate, obtaining 11.4 g of a compound A-51 (a yield: 83%).

EXAMPLE 6: SYNTHESIS OF COMPOUND A-77

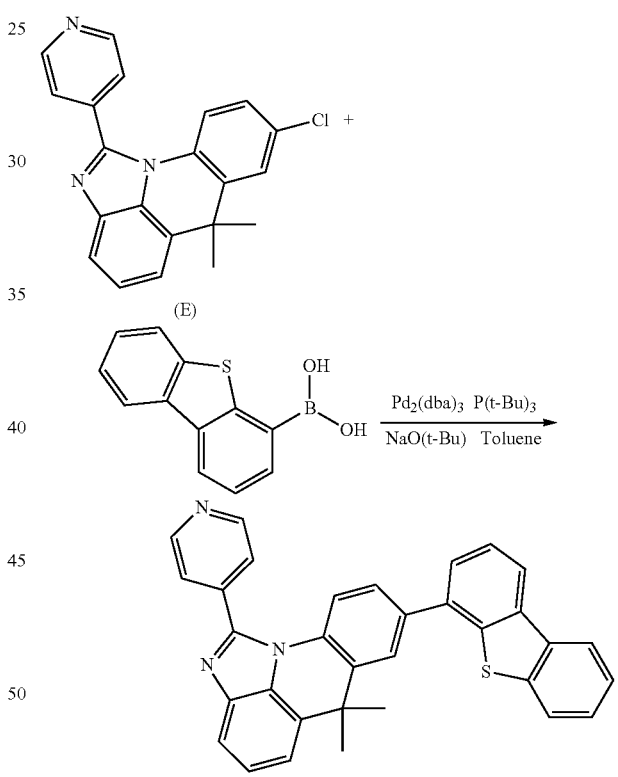

10.0 g (28.92 mmol) of the intermediate product E obtained in the fifth step of Example 5, 7.91 g (34.70 mmol) of 4-dibenzothiophene boronic acid, 5.99 g (43.38 mmol) of $K_2CO_3$, and 0.33 g (0.29 mmmol) of $Pd(PPh_3)_4$ were suspended in 100 ml of toluene and 50 ml of distilled water, and the mixture was refluxed and agitated under a nitrogen stream for 12 hours. When the reaction was complete, the reaction solution was extracted with dichloromethane, filtered with silica gel, distillated under a reduced pressure, silica-columned with hexane:ethylacetate=8:2 (v/v), and recrystallized with dichloromethane and ethylacetate, obtaining 11.4 g of a compound A-77 (a yield: 80%).

EXAMPLE 7: SYNTHESIS OF COMPOUND A-94

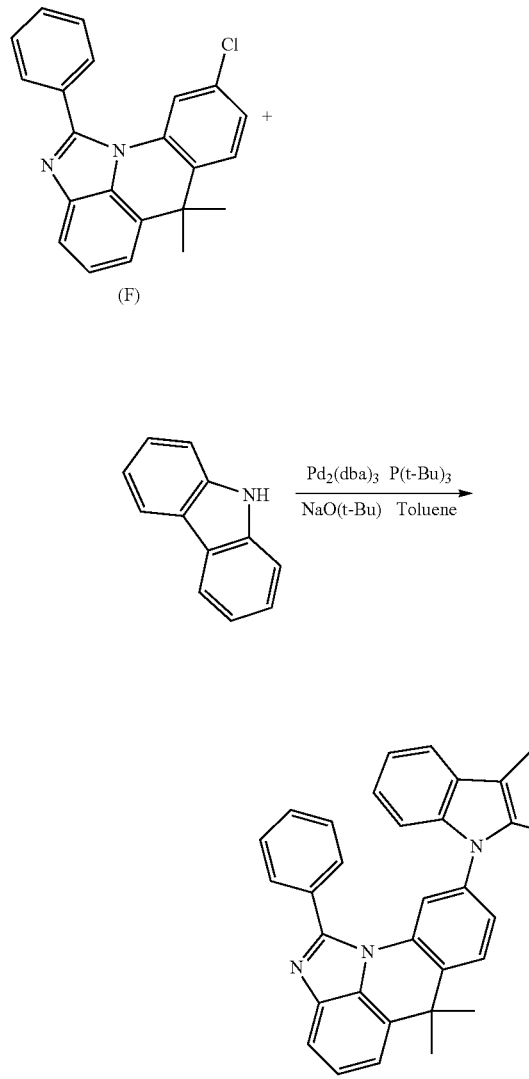

10.0 g (29.00 mmol) of the intermediate product (F) obtained according to the same method as Example 5 except for using benzoaldehyde instead of the pyridine-4-carboaldehyde in the step of Example 5, 5.82 g (34.80 mmol) of carbazole, 4.18 g (43.49 mmol) of NaO(t-Bu), and 0.53 g (0.58 mmmol) of $Pd_2(dba)_3$ were suspended in 150 mL of toluene, 0.28 mL (1.16 mmol) of $P(t-Bu)_3$ was added thereto, and the mixture was refluxed and agitated under a nitrogen stream for 24 hours. The resultant was extracted with dichloromethane and distilled water, and an organic layer therein was silica gel filtered. After removing an organic solution therefrom, the residue was silica gel columned with hexane:ethylacetate=7:3 (v/v) and recrystallized with dichloromethane and ethylacetate, obtaining 11.0 g of a compound A-94 (a yield: 80%).

EXAMPLE 8: SYNTHESIS OF COMPOUND A-74

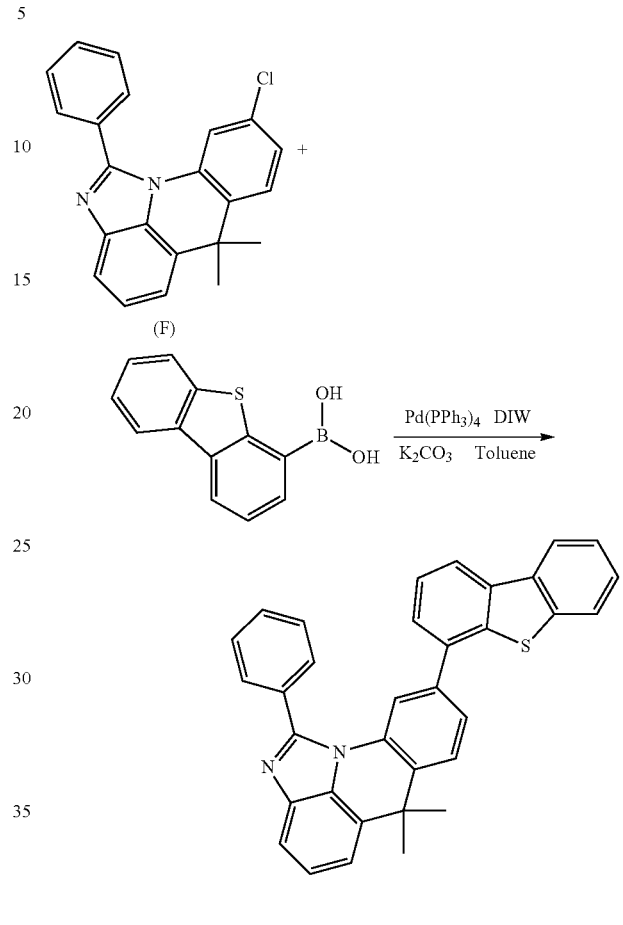

10.0 g (29.00 mmol) of the intermediate product F according to Example 7, 7.94 g (34.80 mmol) of 4-dibenzothiophene boronic acid, 6.01 g (43.50 mmol) of $K_2CO_3$, and 0.34 g (0.29 mmmol) of $Pd(PPh_3)_4$ were suspended in 100 ml of toluene and 50 ml of distilled water, and the suspended resultant was refluxed and agitated under a nitrogen stream for 12 hours. When the reaction was complete, the reaction solution was extracted with dichloromethane, filtered with silica gel, distillated under a reduced pressure, silica column with hexane:ethylacetate=8:2 (v/v), and recrystallized with dichloromethane and ethylacetate, obtaining 12.1 g of a compound A-74 (a yield: 85%).

EXAMPLE 9: SYNTHESIS OF COMPOUND C-17

[Reaction Scheme 3]

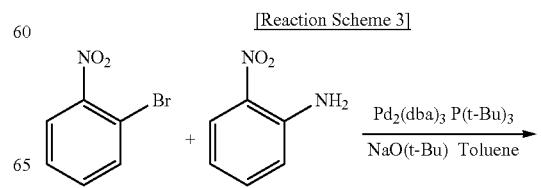

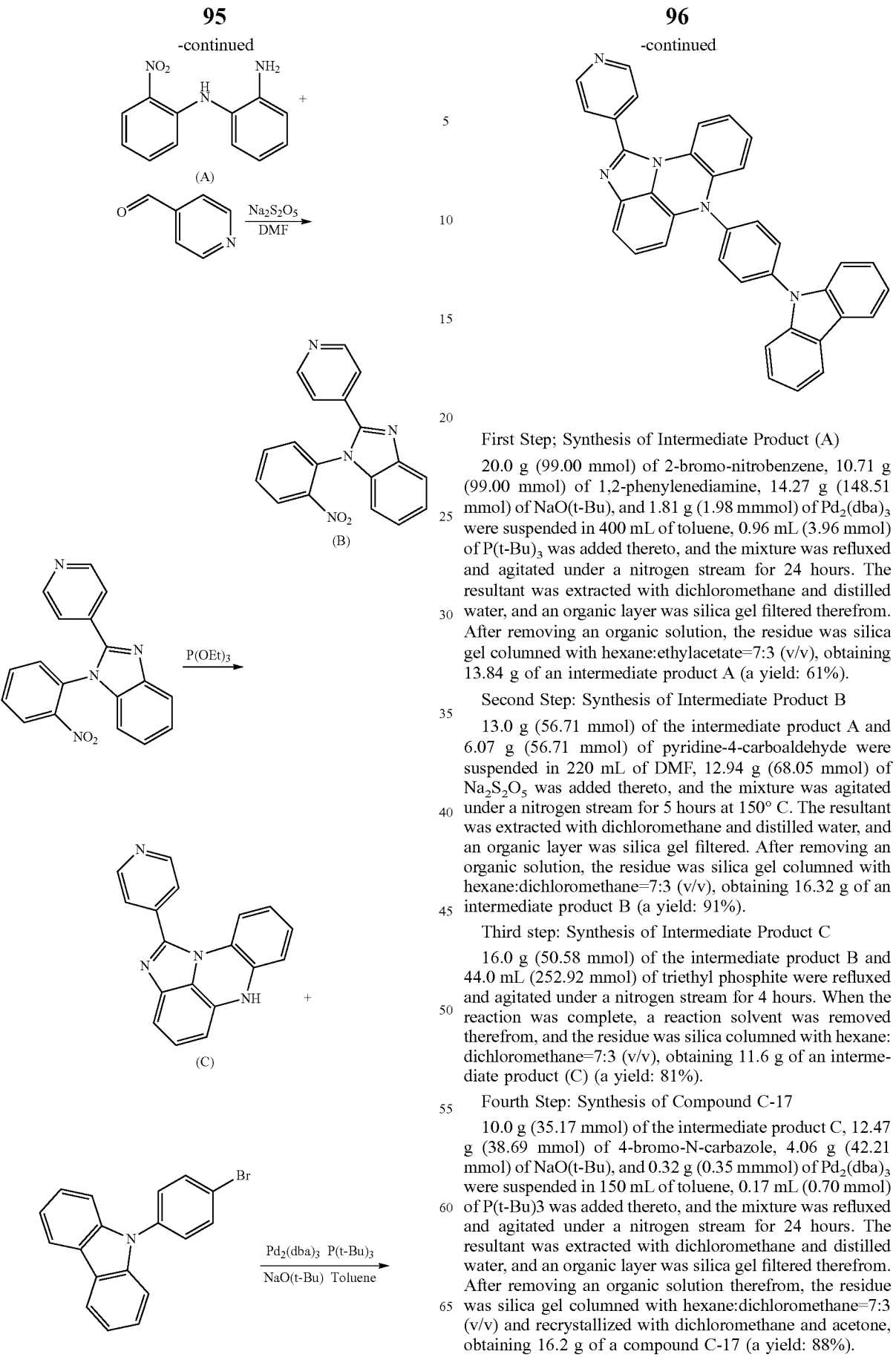

First Step; Synthesis of Intermediate Product (A)

20.0 g (99.00 mmol) of 2-bromo-nitrobenzene, 10.71 g (99.00 mmol) of 1,2-phenylenediamine, 14.27 g (148.51 mmol) of NaO(t-Bu), and 1.81 g (1.98 mmol) of $Pd_2(dba)_3$ were suspended in 400 mL of toluene, 0.96 mL (3.96 mmol) of $P(t-Bu)_3$ was added thereto, and the mixture was refluxed and agitated under a nitrogen stream for 24 hours. The resultant was extracted with dichloromethane and distilled water, and an organic layer was silica gel filtered therefrom. After removing an organic solution, the residue was silica gel columned with hexane:ethylacetate=7:3 (v/v), obtaining 13.84 g of an intermediate product A (a yield: 61%).

Second Step: Synthesis of Intermediate Product B 13.0 g (56.71 mmol) of the intermediate product A and 6.07 g (56.71 mmol) of pyridine-4-carboaldehyde were suspended in 220 mL of DMF, 12.94 g (68.05 mmol) of $Na_2S_2O_5$ was added thereto, and the mixture was agitated under a nitrogen stream for 5 hours at 150° C. The resultant was extracted with dichloromethane and distilled water, and an organic layer was silica gel filtered. After removing an organic solution, the residue was silica gel columned with hexane:dichloromethane=7:3 (v/v), obtaining 16.32 g of an intermediate product B (a yield: 91%).

Third step: Synthesis of Intermediate Product C 16.0 g (50.58 mmol) of the intermediate product B and 44.0 mL (252.92 mmol) of triethyl phosphite were refluxed and agitated under a nitrogen stream for 4 hours. When the reaction was complete, a reaction solvent was removed therefrom, and the residue was silica columned with hexane: dichloromethane=7:3 (v/v), obtaining 11.6 g of an intermediate product (C) (a yield: 81%).

Fourth Step: Synthesis of Compound C-17

10.0 g (35.17 mmol) of the intermediate product C, 12.47 g (38.69 mmol) of 4-bromo-N-carbazole, 4.06 g (42.21 mmol) of NaO(t-Bu), and 0.32 g (0.35 mmmol) of $Pd_2(dba)_3$ were suspended in 150 mL of toluene, 0.17 mL (0.70 mmol) of P(t-Bu)3 was added thereto, and the mixture was refluxed and agitated under a nitrogen stream for 24 hours. The resultant was extracted with dichloromethane and distilled water, and an organic layer was silica gel filtered therefrom. After removing an organic solution therefrom, the residue was silica gel columned with hexane:dichloromethane=7:3 (v/v) and recrystallized with dichloromethane and acetone, obtaining 16.2 g of a compound C-17 (a yield: 88%).

EXAMPLE 10: SYNTHESIS OF COMPOUND C-21

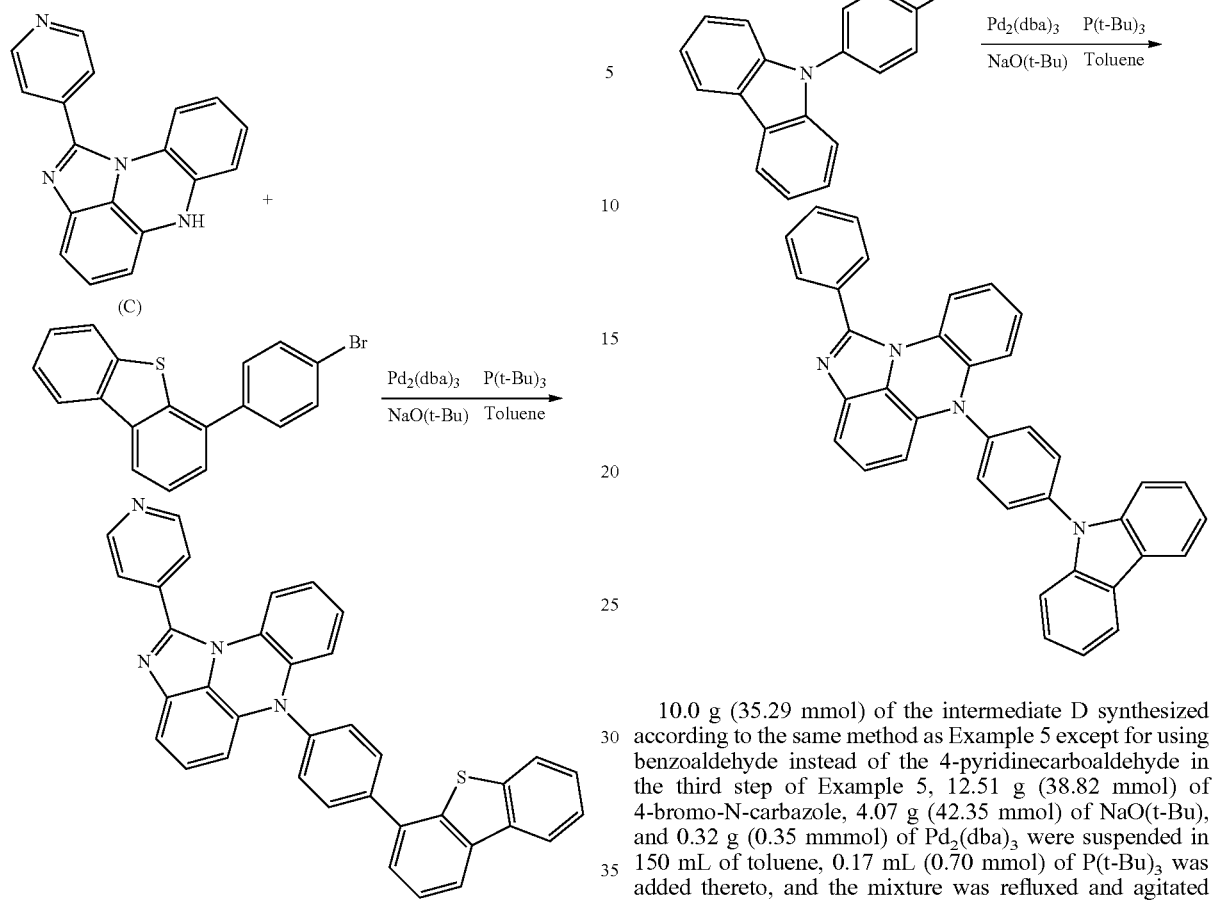

10.0 g (35.17 mmol) of the intermediate product C synthesized in Example 5, 13.13 g (38.69 mmol) of 4-(4-bromophenyl)-dibenzothiophene, 4.06 g (42.21 mmol) of NaO(t-Bu), and 0.32 g (0.35 mmmol) of Pd$_2$(dba)$_3$ were suspended in 150 mL of toluene, 0.17 mL (0.70 mmol) of P(t-Bu)$_3$ was added thereto, and the mixture was refluxed and agitated under a nitrogen stream for 24 hours. The resultant was extracted with dichloromethane and distilled water, and an organic layer was silica gel filtered. After removing an organic solution, the residue was silica gel columned with hexane:dichloromethane=7:3 (v/v) and recrystallized with dichloromethane and acetone, obtaining 16.2 g of a compound C-21 (a yield: 85%).

EXAMPLE 11: SYNTHESIS OF COMPOUND C-11

10.0 g (35.29 mmol) of the intermediate D synthesized according to the same method as Example 5 except for using benzoaldehyde instead of the 4-pyridinecarboaldehyde in the third step of Example 5, 12.51 g (38.82 mmol) of 4-bromo-N-carbazole, 4.07 g (42.35 mmol) of NaO(t-Bu), and 0.32 g (0.35 mmmol) of Pd$_2$(dba)$_3$ were suspended in 150 mL of toluene, 0.17 mL (0.70 mmol) of P(t-Bu)$_3$ was added thereto, and the mixture was refluxed and agitated under a nitrogen stream for 24 hours. The resultant was extracted with dichloromethane and distilled water, and an organic layer was silica gel filtered. After removing an organic solution, the residue was silica gel columned with hexane:dichloromethane=7:3 (v/v) and recrystallized with dichloromethane and acetone, obtaining 16.1 g of a compound C-11 (a yield: 87%).

EXAMPLE 12: SYNTHESIS OF COMPOUND C-15

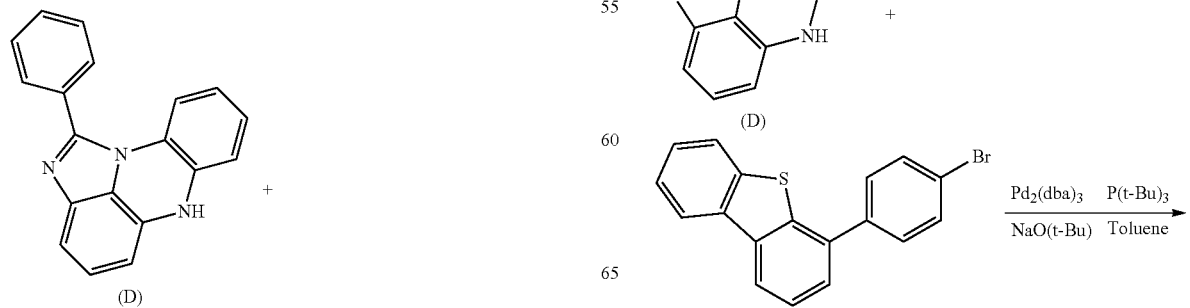

-continued

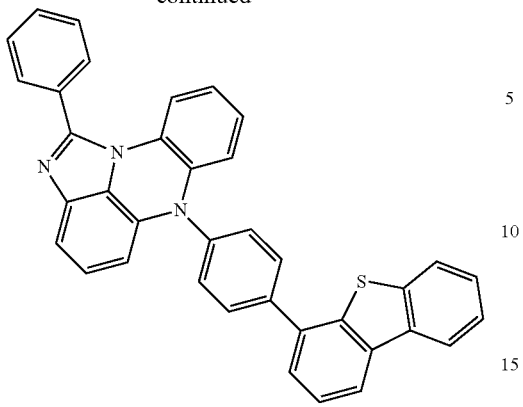

10.0 g (35.29 mmol) of the intermediate D synthesized according to same method as Example 5 except for using benzoaldehyde instead of the 4-pyridinecarboaldehyde in the third step of Example 5, 13.17 g (38.82 mmol) of 4-(4-bromophenyl)-dibenzothiophene, 4.07 g (42.35 mmol) of NaO(t-Bu), and 0.32 g (0.35 mmmol) of Pd$_2$(dba)$_3$ were suspended in 150 mL of toluene, 0.17 mL (0.70 mmol) of P(t-Bu)$_3$ was added thereto, and the mixture was refluxed and agitated under a nitrogen stream for 24 hours. The resultant was extracted with dichloromethane and distilled water, and an organic layer was silica gel filtered. After removing an organic solution, the residue was silica gel columned with hexane:dichloromethane=7:3 (v/v) and then, recrystallized with dichloromethane and acetone, obtaining 15.5 g of a compound C-15 (a yield: 81%).

(Manufacture of Organic Light Emitting Diode)

EXAMPLE 13

A glass substrate coated with ITO (Indium tin oxide) to form a 1500 Å-thick thin film was cleaned with a distilled water ultrasonic wave. After cleaning with distilled water, the glass substrate was ultra sonic wave-cleaned with a solvent such as isopropyl alcohol, acetone, methanol, and the like and moved to a plasma cleaner and then, cleaned by using oxygen plasma for 5 minutes and moved to a vacuum-depositor. This ITO transparent electrode was used as an anode, and HTM (has a material structure as follows) was vacuum-deposited on the ITO substrate to form a 1200 Å-thick hole injection layer.

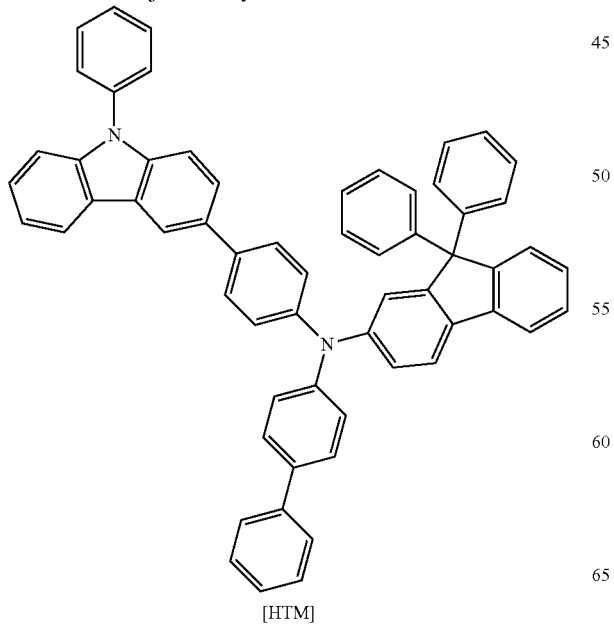

[HTM]

The synthesized material of Example 1 as a host doped with 7 wt % of PhGD (refer to the following structure) as a phosphorescent green dopant were vacuum-deposited on the hole transport layer to form a 300 Å-thick emission layer.

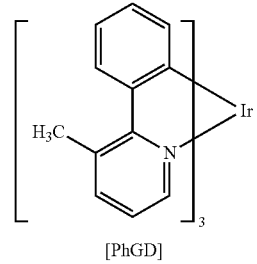

[PhGD]

50 Å-thick BAlq [bis(2-methyl-8-quinolinolato-N1,O8)-(1,1'-biphenyl-4-olato)aluminum] and 250 Å-thick Alq3 [tris (8-hydroxyquinolinato)aluminium] sequentially deposited on the emission layer to form an electron transport layer (ETL). On the electron transport layer (ETL), 10 Å-thick LiF and 1000 Å-thick Al were sequentially vacuum-deposited to form a cathode, manufacturing an organic light emitting diode.

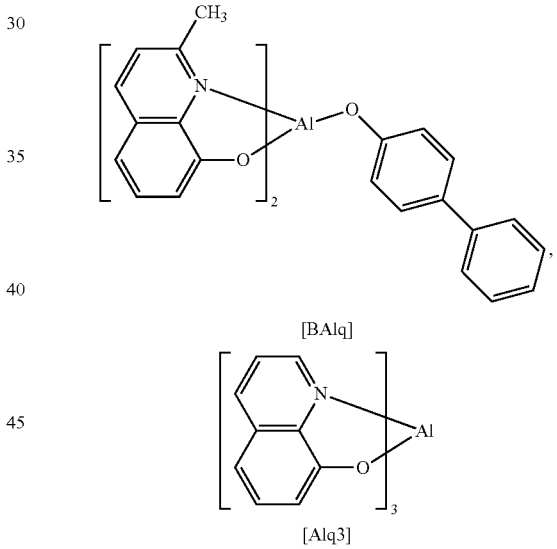

EXAMPLE 14

An organic light emitting diode was manufactured according to the same method as Example 13 except for using the compound B-51 of Example 2 to form the emission layer.

EXAMPLE 15

An organic light emitting diode was manufactured according to the same method as Example 13 except for using the compound B-77 of Example 3 to form the emission layer.

EXAMPLE 16

An organic light emitting diode was manufactured according to the same method as Example 13 except for using the compound B-97 of Example 4 to form the emission layer.

EXAMPLE 17

An organic light emitting diode was manufactured according to the same method as Example 13 except for using the compound A-51 of Example 5 to form the emission layer.

EXAMPLE 18

An organic light emitting diode was manufactured according to the same method as Example 13 except for using the compound A-77 of Example 6 to form the emission layer.

EXAMPLE 19

An organic light emitting diode was manufactured according to the same method as Example 13 except for using the compound A-94 of Example 7 to form the emission layer.

EXAMPLE 20

An organic light emitting diode was manufactured according to the same method as Example 13 except for using the compound A-74 of Example 8 to form the emission layer.

EXAMPLE 21

An organic light emitting diode was manufactured according to the same method as Example 13 except for using the compound C-17 of Example 9 to form the emission layer.

EXAMPLE 22

An organic light emitting diode was manufactured according to the same method as Example 13 except for using the compound C-21 of Example 10 to form the emission layer.

EXAMPLE 23

An organic light emitting diode was manufactured according to the same method as Example 13 except for using the compound C-11 of Example 11 to form the emission layer.

EXAMPLE 24

An organic light emitting diode was manufactured according to the same method as Example 13 except for using the compound C-15 of Example 12 to form the emission layer.

COMPARATIVE EXAMPLE 1

An organic light emitting diode was manufactured according to the same method as Example 1 except for using the following compound according to Comparative Example 1 to form the emission layer.

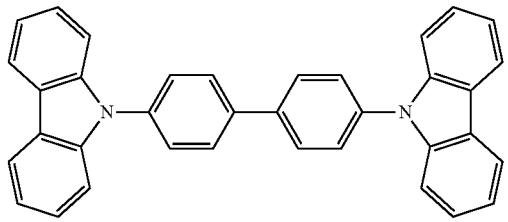 [SMILES: c1ccc2c(c1)c1ccccc1n2-c1ccc(-c2ccc(-n3c4ccccc4c4ccccc43)cc2)cc1]

(Performance Measurement of Organic Light Emitting Diode)

Current density and luminance changes depending on voltage and luminous efficiency of each organic light emitting diode according to 13 to 24 and Comparative Example 1 were measured. Specific measurement methods are as follows, and the results are shown in the following Table 1.

1) Measurement of Current density Change depending on Voltage Change

The manufactured organic light emitting diodes according to 13 to 24 and Comparative Example 1 were measured for current value flowing in the unit device, while increasing the voltage using a current-voltage meter (Keithley 2400), and the measured current value was divided by an area to provide the result.

2) Measurement of Luminance Change depending on Voltage Change

The manufactured organic light emitting diodes according to 13 to 24 and Comparative Example 1 were measured for luminance, while increasing the voltage using a luminance meter (Minolta Cs-1000A).

3) Measurement of Luminous Efficiency and Power Efficiency

The luminance, current density, and voltage obtained from the "1) Measurement of Current density Change depending on Voltage Change" and "2) Measurement of Luminance Change depending on Voltage Change" were used to calculate current efficiency and power efficiency, and the results are shown in Table 2.

4) Color Coordinate

Each organic light emitting diode according to Examples 13 to 24 and Comparative Example 1 was measured regarding a color coordinate at 6000 cd/m$^2$ by using a luminance meter (keithley 2635B).

TABLE 2

| | Luminance 500 cd/m$^2$ | | | | |
|---|---|---|---|---|---|
| | Driving voltage (V) | Luminous efficiency (cd/A) | Power efficiency (lm/W) | CIE x | CIE y |
| Example 13 | 4.40 | 63.76 | 45.50 | 0.322 | 0.631 |
| Example 14 | 4.72 | 61.34 | 40.81 | 0.337 | 0.632 |
| Example 15 | 4.51 | 60.33 | 42.00 | 0.335 | 0.640 |
| Example 16 | 4.88 | 59.74 | 38.44 | 0.340 | 0.627 |
| Example 17 | 4.42 | 62.54 | 44.43 | 0.321 | 0.630 |
| Example 18 | 4.61 | 64.87 | 44.18 | 0.335 | 0.636 |
| Example 19 | 4.77 | 60.97 | 40.14 | 0.333 | 0.639 |
| Example 20 | 4.69 | 60.13 | 40.26 | 0.339 | 0.625 |
| Example 21 | 4.58 | 58.15 | 39.87 | 0.335 | 0.641 |
| Example 22 | 4.78 | 59.53 | 39.11 | 0.336 | 0.621 |
| Example 23 | 4.55 | 57.22 | 39.49 | 0.329 | 0.620 |
| Example 24 | 4.67 | 56.89 | 38.25 | 0.338 | 0.628 |
| Comparative Example 1 | 6.90 | 49.53 | 22.54 | 0.333 | 0.623 |

As shown in Table 2, the organic light emitting diodes according to Examples 13 to 24 showed improved characteristics in terms of a driving voltage, luminous efficiency, and/or power efficiency compared with the organic light emitting diode according to Comparative Example 1.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound represented by the following Chemical Formula 1:

[Chemical Formula 1]

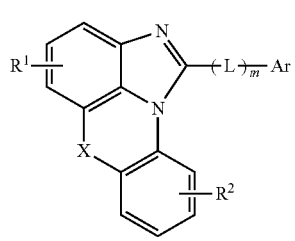

wherein, in Chemical Formula 1,

L is a substituted or unsubstituted C6 to C30 arylene group, or a substituted or unsubstituted C2 to C30 heteroarylene group, m is an integer ranging from 0 to 3, Ar is a substituted or unsubstituted C6 to C30 aryl group or a substituted or unsubstituted C2 to C30 heteroaryl group, X is O, S, $SO_2$ (O=S=O), PO(P=O), NR', CR'R" or SiR'R", R' and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, $R^1$ is hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, when X is O, $SO_2$ (O=S=O), PO(P=O), NR', CR'R" or SiR'R", $R^2$ is hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and when X is S, $R^2$ is a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

2. The compound of claim 1, wherein:
$R^1$ is hydrogen, deuterium, a substituted or unsubstituted C1 to C20 alkyl group, or a substituted or unsubstituted C3 to C40 silyl group, and
Ar is a substituted or unsubstituted C6 to C30 aryl group, or a substituted or unsubstituted C2 to C30 heteroaryl group having electron characteristics.

3. The compound of claim 2, wherein Ar is represented by one of Chemical Formulae ET-1 to ET-3:

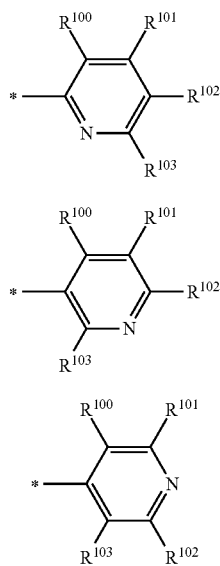

[Chemical Formula ET-1]

[Chemical Formula ET-2]

[Chemical Formula ET-3]

wherein, in Chemical Formulae ET-1 to ET-3,
* indicates a linking position, and
$R^{100}$ to $R^{103}$ are each independently hydrogen, deuterium, a substituted or unsubstituted C1 to C30 alkyl group, a substituted or unsubstituted C6 to C30 aryl group, or a substituted or unsubstituted C2 to C30 heteroaryl group.

4. The compound of claim 2, wherein Ar is represented by one of Chemical Formulae ET-4 to ET-6:

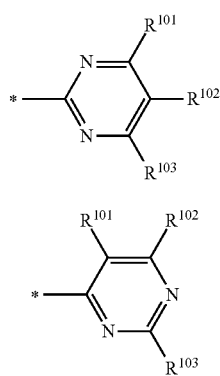

[Chemical Formula ET-4]

[Chemical Formula ET-5]

[Chemical Formula ET-6]

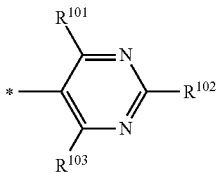

wherein, in Chemical Formulae ET-4 to ET-6,
* indicates a linking position, and
$R^{101}$ to $R^{103}$ are each independently hydrogen, deuterium, a substituted or unsubstituted C1 to C30 alkyl group, a substituted or unsubstituted C6 to C30 aryl group, or a substituted or unsubstituted C2 to C30 heteroaryl group.

5. The compound of claim 2, wherein Ar is represented by Chemical Formula ET-7:

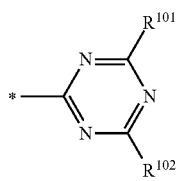

[Chemical Formula ET-7]

wherein, in Chemical Formula ET-7,
* indicates a linking position, and
$R^{101}$ and $R^{102}$ are each independently hydrogen, deuterium, a substituted or unsubstituted C1 to C30 alkyl group, a substituted or unsubstituted C6 to C30 aryl group, or a substituted or unsubstituted C2 to C30 heteroaryl group.

6. The compound of claim 1, wherein X is NR' or CR'R", in which R' and R" are each independently hydrogen, deuterium, a substituted or unsubstituted C1 to C20 alkyl group, a substituted or unsubstituted C6 to C30 aryl group, or a substituted or unsubstituted C2 to C30 heteroaryl group.

7. The compound of claim 6, wherein R' is a group represented by Chemical Formula X-1:

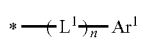

[Chemical Formula X-1]

wherein, in Chemical Formula X-1,
* indicates a linking position,
$L^1$ is a substituted or unsubstituted C6 to C30 arylene group, or a substituted or unsubstituted C2 to C30 heteroarylene group,
n is an integer ranging from 0 to 3, and
$Ar^1$ is a substituted or unsubstituted C6 to C30 aryl group or a substituted or unsubstituted C2 to C30 heteroaryl group.

8. The compound of claim 7, wherein the group represented by Chemical Formula X-1 is represented by Chemical Formula X-2 or Chemical Formula X-3:

[Chemical Formula X-2]

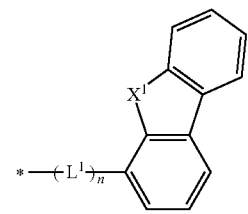

[Chemical Formula X-3]

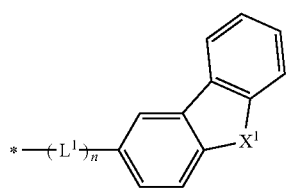

[Chemical Formula X-4]

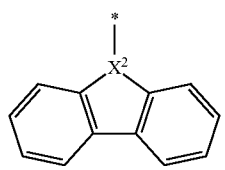

[Chemical Formula X-5]

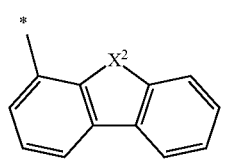

[Chemical Formula X-6]

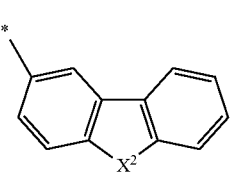

wherein, in Chemical Formulae X-2 and X-3,

* indicates a linking position, $L^1$ is a substituted or unsubstituted C6 to C30 arylene group, or a substituted or unsubstituted C2 to C30 heteroarylene group, n is an integer ranging from 0 to 3, and $X^1$ is NR', O, or S, in which R' is hydrogen, deuterium, a substituted or unsubstituted C1 to C20 alkyl group, a substituted or unsubstituted C6 to C30 aryl group, or a substituted or unsubstituted C2 to C30 heteroaryl group.

9. The compound of claim 1, wherein:

X is O, $SO_2$ (O=S=O), PO(P=O), NR', CR'R" or SiR'R", $R^1$ is hydrogen, deuterium, a substituted or unsubstituted C1 to C10 alkyl group, or a substituted or unsubstituted silyl group, and $R^2$ is hydrogen, deuterium, a substituted or unsubstituted C1 to C20 alkyl group, a substituted or unsubstituted C6 to C30 aryl group, or a substituted or unsubstituted C2 to C30 heteroaryl group, or X is S $R^1$ is hydrogen, deuterium, a substituted or unsubstituted C1 to C10 alkyl group, or a substituted or unsubstituted silyl group, and $R^2$ is a substituted or unsubstituted C1 to C20 alkyl group, a substituted or unsubstituted C6 to C30 aryl group, or a substituted or unsubstituted C2 to C30 heteroaryl group.

10. The compound of claim 9, wherein:

$R^2$ is the substituted or unsubstituted C6 to C30 aryl group, and the substituted or unsubstituted C6 to C30 aryl group is a substituted or unsubstituted phenyl group, a substituted or unsubstituted naphthyl group, a substituted or unsubstituted biphenyl group, a substituted or unsubstituted anthracenyl group, a substituted or unsubstituted phenanthryl group, or a substituted or unsubstituted triphenylenyl group.

11. The compound of claim 9, wherein:

$R^2$ is the substituted or unsubstituted C2 to C30 heteroaryl group, and the substituted or unsubstituted C2 to C30 heteroaryl group is represented by one of Chemical Formula X-4 to Chemical Formula X-6:

wherein, in Chemical Formulae X-4 to X-6, * indicates a linking position, in Chemical Formula X-4, $X^2$ is N, and in Chemical Formulae X-5 and X-6, $X^2$ is NR', O or S, in which R' is hydrogen, deuterium, a substituted or unsubstituted C1 to C20 alkyl group, a substituted or unsubstituted C6 to C30 aryl group, or a substituted or unsubstituted C2 to C30 heteroaryl group.

12. The compound of claim 9, wherein:

$R^2$ is the substituted or unsubstituted C2 to C30 heteroaryl group, and the substituted or unsubstituted C2 to C30 heteroaryl group is represented by Chemical Formula X-7:

[Chemical Formula X-7]

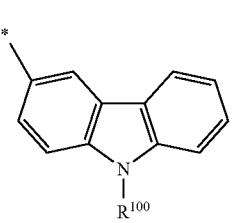

wherein, in Chemical Formula X-7,

* indicates a linking position, and $R^{100}$ is a substituted or unsubstituted C1 to C30 alkyl group, or a substituted or unsubstituted C6 to C30 aryl group.

13. The compound of claim 1, wherein the compound represented by Chemical Formula 1 is represented by Chemical Formula A-51, A-74, A-77, A-94, B-51, B-77, B-94, B-97, C-11, C-15, C-17, or C-21:

-continued
[A-51]
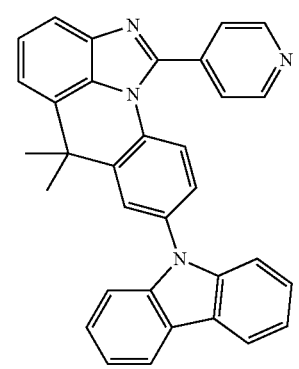
[B-51]
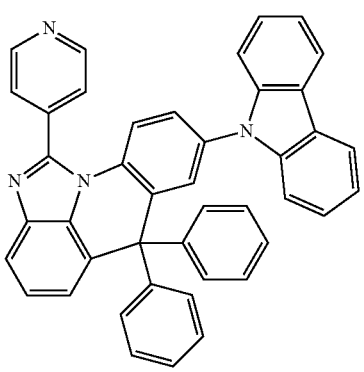
[A-74]
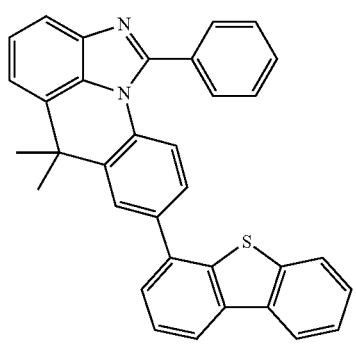
[B-77]
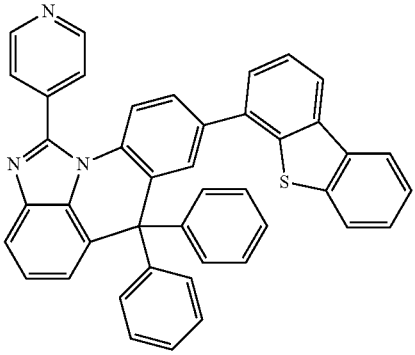
[A-77]
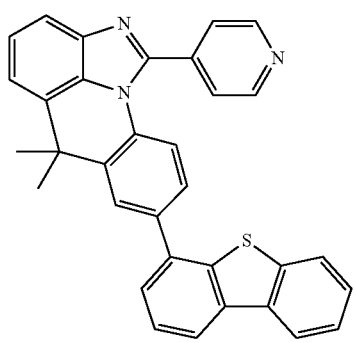
[B-94]
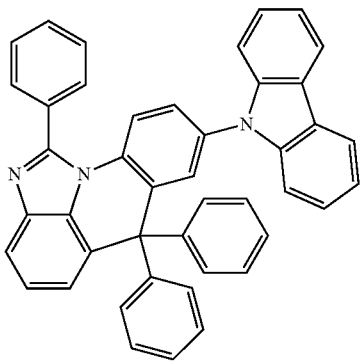
[A-94]
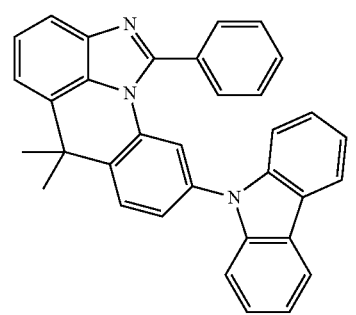
[B-97]
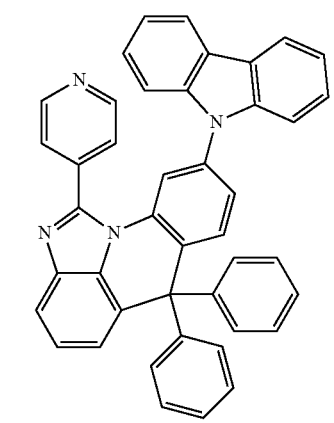

111
-continued

[C-11]
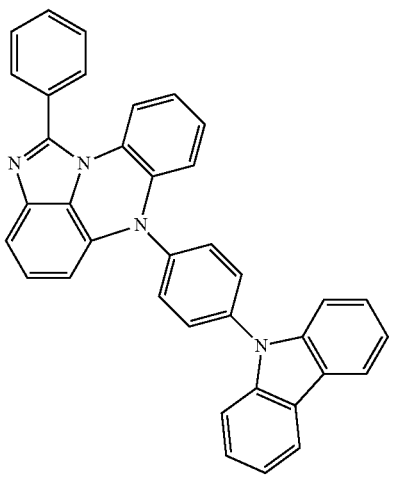

[C-15]
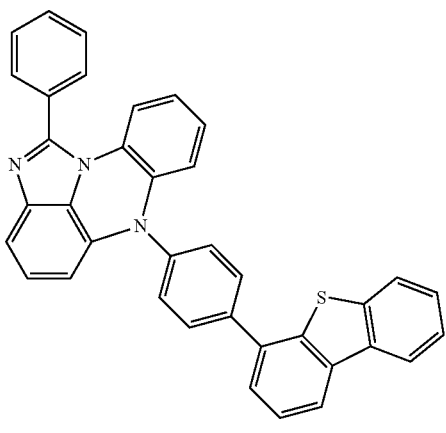

[C-17]
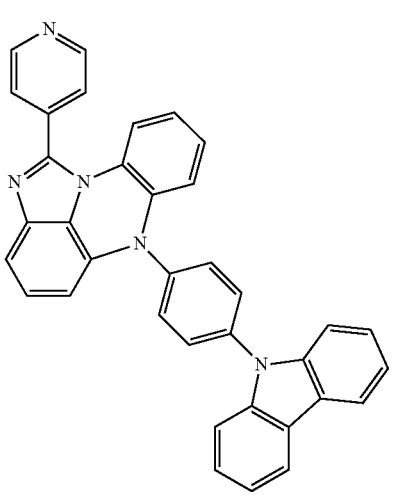

112
-continued

[C-21]
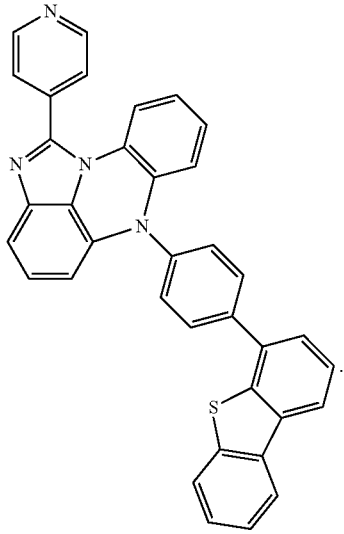

14. The compound of claim 1, wherein the compound has a triplet exciton energy (T1) of 2.0 eV or greater.

15. An organic optoelectronic device, comprising:
an anode and a cathode facing each other; and
at least one organic thin layer interposed between the anode and cathode,
wherein the organic layer includes a compound represented by the following Chemical Formula 1:

Chemical Formula 1
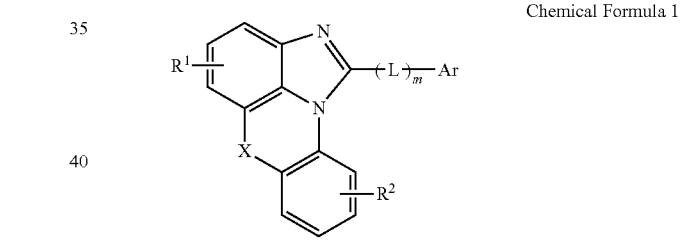

wherein, in Chemical Formula 1,
L is a substituted or unsubstituted C6 to C30 arylene group, or a substituted or unsubstituted C2 to C30 heteroarylene group,
m is an integer ranging from 0 to 3,
Ar is a substituted or unsubstituted C6 to C30 aryl group or a substituted or unsubstituted C2 to C30 heteroaryl group,
X is O, S, SO$_2$ (O=S=O), PO(P=O), NR', CR'R" or SiR'R",
R' and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $R^1$ and $R^2$ are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof.

16. The organic optoelectronic device of claim 15, wherein the organic layer comprises an emission layer.

17. The organic optoelectronic device of claim 16, wherein the compound is a host in the emission layer.

18. The organic optoelectronic device of claim 16, wherein the compound is a green phosphorescent host in the emission layer.

19. The organic optoelectronic device of claim 15, wherein:
the organic layer comprises at least one auxiliary layer selected from a hole injection layer, a hole transport layer, an electron blocking layer, an electron transport layer, an electron injection layer, and a hole blocking layer, and
the at least one auxiliary layer comprises the compound.

20. A display device including the organic light emitting diode of claim 15.

* * * * *